US008293277B2

(12) United States Patent
Swanson et al.

(10) Patent No.: US 8,293,277 B2
(45) Date of Patent: Oct. 23, 2012

(54) CONTROLLED-RELEASE NANOPARTICULATE COMPOSITIONS

(75) Inventors: Jon Swanson, North Wales, PA (US); Rajeev A. Jain, Framingham, MA (US); Robert Hontz, Newton Square, PA (US); John G. Devane, Athlone (IE); Kenneth Iain Cumming, Essex (GB); Maurice Joseph Anthony Clancy, Dublin (IE); Janet Elizabeth Codd, Athlone (IE); Gary Liversidge, Westchester, PA (US)

(73) Assignee: Alkermes Pharma Ireland Limited, Dublin (IE)

( * ) Notice: Subject to any disclaimer, the term of this patent is extended or adjusted under 35 U.S.C. 154(b) by 0 days.

(21) Appl. No.: 09/337,675

(22) Filed: Jun. 22, 1999

(65) Prior Publication Data

US 2002/0012675 A1   Jan. 31, 2002

Related U.S. Application Data

(63) Continuation-in-part of application No. 09/164,351, filed on Oct. 1, 1998, now abandoned.

(51) Int. Cl.
*A61K 9/16* (2006.01)
*A61K 9/20* (2006.01)
*A61K 9/22* (2006.01)
*A61K 9/26* (2006.01)

(52) U.S. Cl. ........ 424/490; 424/464; 424/465; 424/468; 424/469; 424/470

(58) Field of Classification Search .................. 424/464, 424/468, 474, 469, 472, 489, 451, 457, 467, 424/478, 481, 484, 490
See application file for complete search history.

(56) References Cited

U.S. PATENT DOCUMENTS

| 3,269,798 | A |   | 8/1966  | Preston |
| 3,692,532 | A |   | 9/1972  | Shankenberg et al. |
| 4,225,581 | A |   | 9/1980  | Kreuter et al. |
| 4,389,397 | A |   | 6/1983  | Lo et al. |
| 4,524,060 | A | * | 6/1985  | Mughal et al. ............... 424/459 |
| 4,540,602 | A |   | 9/1985  | Motoyama et al. |
| 4,562,069 | A |   | 12/1985 | Hegasy et al. |
| 4,657,901 | A |   | 4/1987  | Ueda et al. |
| 4,665,081 | A | * | 5/1987  | Doi et al. ..................... 514/356 |
| 4,727,077 | A |   | 2/1988  | Haga et al. .................. 514/274 |
| 4,757,059 | A |   | 7/1988  | Sorenson |
| 4,765,990 | A | * | 8/1988  | Sugimoto et al. ............ 424/494 |
| 4,783,484 | A |   | 11/1988 | Violante et al. ............. 514/535 |
| 4,814,175 | A |   | 3/1989  | Tack et al. |
| 4,826,689 | A |   | 5/1989  | Violante et al. ............. 424/489 |
| 4,851,421 | A |   | 7/1989  | Iwasaki et al. .............. 514/352 |
| 4,863,742 | A |   | 9/1989  | Panoz et al. |
| 4,880,634 | A |   | 11/1989 | Speiser |
| 4,895,726 | A | * | 1/1990  | Curtet et al. ................. 424/456 |
| 4,904,668 | A |   | 2/1990  | Kondo et al. ................ 514/274 |
| 4,917,816 | A |   | 4/1990  | Self |
| 4,983,605 | A |   | 1/1991  | Kondo et al. ................ 514/247 |
| 4,997,454 | A |   | 3/1991  | Violante et al. ............. 23/305 A |
| 5,002,952 | A |   | 3/1991  | Kondo et al. ................ 514/274 |
| 5,049,322 | A |   | 9/1991  | Devissaguet et al. |
| 5,098,907 | A |   | 3/1992  | Kondo et al. ................ 514/274 |
| 5,110,605 | A |   | 5/1992  | Acharya ...................... 424/487 |
| 5,118,528 | A |   | 6/1992  | Fessi et al. |
| 5,133,908 | A |   | 7/1992  | Stainmesse et al. |
| 5,145,684 | A | * | 9/1992  | Liversidge et al. .......... 424/489 |
| 5,156,767 | A | * | 10/1992 | Fitzgerald et al. ........... 516/136 |
| 5,188,755 | A | * | 2/1993  | Chang |
| 5,215,758 | A |   | 6/1993  | Krishnamurthy ............. 424/488 |
| 5,260,478 | A |   | 11/1993 | Bacon et al. ................. 560/110 |
| 5,264,213 | A |   | 11/1993 | Shibahara et al. ........... 424/409 |
| 5,264,610 | A |   | 11/1993 | Bacon ............................ 560/47 |
| 5,298,262 | A |   | 3/1994  | Na et al. |
| 5,300,739 | A |   | 4/1994  | Bittar .......................... 187/127 |
| 5,302,401 | A |   | 4/1994  | Liversidge et al. |
| 5,318,767 | A |   | 6/1994  | Liversidge et al. |
| 5,336,507 | A |   | 8/1994  | Na et al. |
| 5,338,761 | A |   | 8/1994  | Nakajima et al. |
| 5,356,467 | A |   | 10/1994 | Oshlack et al. |
| 5,384,124 | A |   | 1/1995  | Courteille et al. |
| 5,399,363 | A |   | 3/1995  | Liversidge et al. |
| 5,447,710 | A |   | 9/1995  | Na et al. |
| 5,466,440 | A |   | 11/1995 | Ruddy et al. |
| 5,510,118 | A |   | 4/1996  | Swanson et al. |
| 5,518,738 | A |   | 5/1996  | Eickhoff et al. |
| 5,521,168 | A |   | 5/1996  | Clark |
| 5,552,160 | A | * | 9/1996  | Liversidge et al. .......... 424/489 |
| 5,573,783 | A | * | 11/1996 | Desieno et al. ............. 424/490 |
| 5,585,108 | A |   | 12/1996 | Ruddy et al. |

(Continued)

FOREIGN PATENT DOCUMENTS

CA        2346001         4/2000

(Continued)

OTHER PUBLICATIONS

Rong-Kun Chang, "Sustained Drug Release from Tablets and Particles Through Coating", Pharmaceutical Dosage Forms, 1990, pp. 199-302.*
Kondo et al., "Improved Oral Absorption of Enteric Coprecipitates of a Poorly Soluble Drug," *J. Pharm. Sciences*, 83(4):566-570 (1994).
Kondo et al., "Improved Oral Absorption of a Poorly Water-Soluble Drug, HO-221, by Wet-Bead Milling Producing Particles in Submicron Region," *Chem. Pharm. Bull.*, 41(4):737-740 (1993).
Kondo, et al, "Pharmacokinetics of a Micronized, Poorly Water Soluble Drug, HO-221, in Experimental Animals," *Biol. Pharm. Bull.*, 16(8):796-800 (1993).

(Continued)

*Primary Examiner* — Susan Tran
(74) *Attorney, Agent, or Firm* — Foley & Lardner LLP

(57) ABSTRACT

Described are controlled release nanoparticulate formulations comprising a nanoparticulate agent to be administered and a rate-controlling polymer which functions to prolong the release of the agent following administration. The novel compositions release the agent following administration for a time period ranging from about 2 to about 24 hours or longer.

28 Claims, 12 Drawing Sheets

U.S. PATENT DOCUMENTS

| | | | |
|---|---|---|---|
| 5,595,762 A | 1/1997 | Derrieu et al. | |
| 5,656,299 A | 8/1997 | Kino et al. | |
| 5,741,522 A | 4/1998 | Violante et al. | 424/489 |
| 5,776,496 A | 7/1998 | Violante et al. | 424/489 |
| 5,795,909 A | 8/1998 | Shashoua et al. | |
| 5,811,388 A * | 9/1998 | Friend et al. | 514/2 |
| 5,811,404 A | 9/1998 | De Frees et al. | 514/25 |
| 5,811,422 A | 9/1998 | Lam et al. | 514/218 |
| 5,811,425 A | 9/1998 | Woods et al. | 514/249 |
| 5,853,756 A * | 12/1998 | Mody et al. | 424/451 |
| 5,871,747 A | 2/1999 | Gengoux-Sedlik et al. | |
| 5,889,088 A | 3/1999 | Kisuno et al. | |
| 5,916,596 A | 6/1999 | Desai et al. | |
| 5,939,091 A | 8/1999 | Eoga et al. | |
| 5,972,389 A * | 10/1999 | Shell et al. | 424/501 |
| 6,001,928 A * | 12/1999 | Harkness et al. | 524/858 |
| 6,004,582 A | 12/1999 | Faour et al. | |
| 6,017,932 A | 1/2000 | Singh et al. | |
| 6,045,829 A | 4/2000 | Liversidge et al. | |
| 6,068,858 A | 5/2000 | Liversidge et al. | |
| 6,093,420 A * | 7/2000 | Baichwal | 424/468 |
| 6,177,103 B1 | 1/2001 | Pace et al. | |
| 6,177,104 B1 | 1/2001 | Allen et al. | |
| 6,193,960 B1 | 2/2001 | Metzger et al. | |
| 6,231,888 B1 | 5/2001 | Lerner et al. | |
| 6,316,029 B1 | 11/2001 | Jain et al. | |
| 6,368,620 B2 | 4/2002 | Liu et al. | |
| 6,375,986 B1 | 4/2002 | Ryde et al. | |
| 6,395,300 B1 | 5/2002 | Straub et al. | |
| 6,458,373 B1 | 10/2002 | Lambert et al. | |
| 6,458,777 B1 | 10/2002 | Sonis et al. | |
| 6,592,903 B2 | 7/2003 | Ryde et al. | |
| 6,696,084 B2 | 2/2004 | Pace et al. | |
| 7,198,795 B2 | 4/2007 | Cooper et al. | |
| 2002/0002294 A1 | 1/2002 | Cushman | |
| 2002/0055462 A1 | 5/2002 | Reed et al. | |
| 2002/0165265 A1 | 11/2002 | Hunter et al. | |
| 2003/0077329 A1 | 4/2003 | Kipp et al. | |
| 2004/0033267 A1 | 2/2004 | Merisko-Liversidge et al. | |
| 2004/0198644 A1 | 10/2004 | Bender et al. | |
| 2005/0004049 A1 | 1/2005 | Liversidge et al. | |
| 2007/0048378 A1 * | 3/2007 | Swanson et al. | 424/469 |
| 2007/0160675 A1 | 7/2007 | Devane et al. | |

FOREIGN PATENT DOCUMENTS

| | | |
|---|---|---|
| EP | 0 220 143 | 4/1987 |
| EP | 0 220 760 B1 | 5/1987 |
| EP | 0 262 560 A2 | 9/1987 |
| EP | 0 275 796 | 7/1988 |
| EP | 0 375 662 | 6/1990 |
| EP | 0 486 153 A2 | 5/1992 |
| EP | 0 499 299 | 8/1992 |
| EP | 0 577 215 | 1/1994 |
| EP | 0 600 532 A2 | 6/1994 |
| EP | 0 601 619 A2 | 6/1994 |
| EP | 0 602 702 A1 | 6/1994 |
| EP | 0 577 215 | 3/2000 |
| EP | 1 010 435 A1 | 6/2000 |
| EP | 1 800 666 A1 | 6/2007 |
| FR | 2304326 | 10/1976 |
| GB | 2 166 651 A | 5/1986 |
| JP | 48-043848 | 11/1970 |
| JP | 57-26615 | 2/1982 |
| JP | 61-218516 | 9/1986 |
| JP | 62-126127 | 6/1987 |
| JP | 63-005021 | 1/1988 |
| JP | 2-167222 | 6/1990 |
| JP | 03/066613 | 3/1991 |
| JP | 4-502318 | 4/1992 |
| JP | 4-295420 | 10/1992 |
| JP | 6-227967 | 8/1994 |
| JP | 07-112936 | 5/1995 |
| JP | 8-151322 | 6/1996 |
| JP | 8-507075 | 7/1996 |
| JP | 8-259460 | 10/1996 |
| JP | 9-241178 | 9/1997 |
| JP | 09-271658 | 10/1997 |
| JP | 2004-513886 | 5/2004 |
| WO | WO 90/15593 | 12/1990 |
| WO | WO 91/13612 | 9/1991 |
| WO | WO 93-10760 | 6/1993 |
| WO | WO 93/10760 | 6/1993 |
| WO | WO 93/10767 | 6/1993 |
| WO | WO 93/13773 | 7/1993 |
| WO | WO 93/25190 | 12/1993 |
| WO | WO 93/25194 | 12/1993 |
| WO | WO 93/25195 | 12/1993 |
| WO | WO 94/18954 | 9/1994 |
| WO | WO 94/20072 | 9/1994 |
| WO | WO 95/05164 | 2/1995 |
| WO | WO 95/22318 * | 8/1995 |
| WO | WO 95/22318 A1 * | 8/1995 |
| WO | WO 95/27475 | 10/1995 |
| WO | WO 96/20698 | 7/1996 |
| WO | WO 96/20698 A2 | 7/1996 |
| WO | WO 9620698 A2 * | 7/1996 |
| WO | WO 96/24335 | 8/1996 |
| WO | WO 96/25918 | 8/1996 |
| WO | WO 97/18796 | 5/1997 |
| WO | WO 98/04291 | 2/1998 |
| WO | WO 98/07414 | 2/1998 |
| WO | WO 98/14174 | 4/1998 |
| WO | WO 98/29098 | 7/1998 |
| WO | WO 98/35666 | 8/1998 |
| WO | WO 99/02665 | 1/1999 |
| WO | WO 9902665 A1 * | 1/1999 |
| WO | WO 99/25354 | 5/1999 |
| WO | WO 99/38493 | 8/1999 |
| WO | WO 99/65469 | 12/1999 |
| WO | WO 00/13672 | 3/2000 |
| WO | WO 00/18374 | 4/2000 |
| WO | WO 00/32189 | 6/2000 |
| WO | WO 00/47196 | 8/2000 |
| WO | WO 00/51572 | 9/2000 |
| WO | WO 0053164 | 9/2000 |
| WO | WO 01/17546 A1 | 3/2001 |
| WO | WO 01/26635 | 4/2001 |
| WO | WO 01/78505 A1 | 10/2001 |
| WO | WO 01/78680 A2 | 10/2001 |
| WO | WO 01/91750 A1 | 12/2001 |
| WO | WO 01/92584 A1 | 12/2001 |
| WO | WO 02/24163 | 3/2002 |
| WO | WO 02/067901 A1 | 9/2002 |
| WO | WO 03/080027 A1 | 10/2003 |
| WO | WO 03/094894 A1 | 11/2003 |
| WO | WO 03/103633 A1 | 12/2003 |
| WO | WO 01/45674 | 6/2011 |

OTHER PUBLICATIONS

Guidance for Industry, Levothyroxine Sodium Tablets—in Vivo Pharmacokinetic and Bioavailability Studies and in vitro Dissolution Testing, Dec. 2000, pp. 1-8.

Office Action dated Mar. 13, 2009 from related U.S. Appl. No. 11/979,231, 15 pgs.

Office Action dated Nov. 12, 2008 for related U.S. Appl. No. 10/667,470, 20 pgs.

Office Action dated Oct. 16, 2008 for related U.S. Appl. No. 11/898,274, 13 pgs.

Office Action dated Sep. 18, 2008 for related U.S. Appl. No. 11/979,231, 11 pgs.

Notice of Reasons for Rejection cited in related Japanese Patent Application No. 2002-528199, Oct. 30, 2008, 3 pgs.

Office Action for related U.S. Appl. No. 12/078,027, dated Dec. 12, 2008, 12 pgs.

Notice of Rejections for Japanese Patent Application No. 2001-529425, dated Jan. 6, 2009, 5 pgs.

Calvo et al., "Development of Positively Charged Colloidal Drug Carriers: Chitosan-Coated Polyester nanocapsules and Submicron-Emulsions," Colloid. Polym. Sci., 275, pp. 46-53 (1997).

Rock et al., "Control of Calcium Carbonate Particle Size and Shape by Precipitation from CTAB/Alcohol/Hexadecane Mixtures," Colloid. Polym. Sci., 275, pp. 893-896 (1997).

Notice of Rejections for Japanese Patent Application No. 2001-583733, dated Jan. 6, 2009., 5 pgs.

Office Action cited in related U.S. Appl. No. 10/667,470, dated Dec. 29, 2009.
Office Action cited in related U.S. Appl. No. 11/979,240, dated Dec. 16, 2009.
Notice of Reasons for Rejection cited in related Japanese Patent Application No. 2004-510760 dated Dec. 2, 2009, 4 pgs.
Notice of Reasons for Rejection cited in related Japanese Patent Application No. 2004-521891 dated Dec. 22, 2009, 3 pgs.
Notice of Reasons for Rejection cited in related Japanese Patent Application No. 2003-565446, dated Jan. 20, 2010, 4 pgs.
Office Action cited in related U.S. Appl. No. 11/979,231, dated Mar. 16, 2010.
Office Action cited in related U.S. Appl. No. 11/980,720, dated Mar. 29, 2010.
Butler et al., "Effects of Protein Stabilizing Agents on Thermal Backbone Motions: A Disulfide Trapping Study," *Biochemistry*, vol. 35, pp. 10595-10600 (1996).
Canadian Office Action for related Canadian Patent Application No. 2,488,499, dated Feb. 8, 2010.
Office Action cited in related U.S. Appl. No. 10/697,703, dated Feb. 18, 2010.
Decision on Rejection cited in related Japanese Patent Application No. 2001-583733, dated Jun. 9, 2010, 3 pgs.
"Design and Evaluation of Oral Administration Drug Formulation", *Pharmaceutical Industry Time Signal Company*, pp. 167-168 (1995).
Office Action cited in related U.S. Appl. No. 11/898,274 dated May 5, 2009.
Office Action cited in related U.S. Appl. No. 10/677,857 dated Jul. 8, 2009.
Office Action cited in related U.S. Appl. No. 10/697,703 dated Jul. 9, 2009.
Office Action cited in related U.S. Appl. No. 10/667,470 dated May 19, 2009.
Office Action cited in related U.S. Appl. No. 10/697,716 dated Apr. 15, 2009.
Canadian Office Action dated Jul. 6, 2010 cited in related Canadian Patent Application No. 2,492,488, 3 pgs.
Office Action cited in related U.S. Appl. No. 11/650,412, dated May 12, 2009.
Notice of Rejections completed Aug. 24, 2009 for related Japanese Patent Application No. 2002-590934, and Notice of Rejections completed Apr. 24, 2008 listing documents A1-A10 and prior art references 1-5.
Notice of Rejections completed Aug. 26, 2009 for related Japanese Patent Application No. 2001-583733.
Matsumoto et al., "Physical Properties of Solid Molecular dispersions of Indomethacin with Poly(vinylpyrrolidone) and Poly(vinylpyrrolidone-co-vinyl-acetate) in Relation to Indomethacin Crystallization," *Pharmaceutical Research* (1999), vol. 16, No. 11, pp. 1722-1728, XP000987250.
Hülsmann et al., "Melt extrusion—an alternative method for enhancing the dissolution rate of 17β—estradiol hemihydrate," *European Journal of Pharmaceutics and Biopharmaceutics* (2000), vol. 49, No. 3, pp. 237-242, XP004257163.
Vojnovic et al., "Formulation and evaluation of vinylpyrrolidone/vinylacetate copolymer microspheres and griseofulvin," *J. Microencapsulation* (1993), vol. 10, No. 1, pp. 89-99, XP000334996.
Bogdanova et al., "Solid Dispersions of Isopropylantipyrin," *Labo-Pharma-Probl. Tech.* (1984), vol. 32, No. 348, pp. 835-837, XP001097528.
Zingone et al., "Characterization and dissolution study of solid dispersions of theophylline and indomethacin with PVP/VA copolymers," *STP Pharma Sciences* (1992), vol. 2, No. 2, pp. 186-192, XP002111752.
Office Action cited in related U.S. Appl. No. 10/619,539 dated Sep. 8, 2009.
Office Action cited in related U.S. Appl. No. 11/979,231 dated Sep. 16, 2009.
Office Action cited in related U.S. Appl. No. 10/697,716 dated Sep. 15, 2009.
Office Action cited in related U.S. Appl. No. 10/701,064, dated Nov. 23, 2009.
Office Action cited in related U.S. Appl. No. 11/898,274, dated Oct. 23, 2009.
Office Action cited in related U.S. Appl. No. 11/980,720, dated Oct. 5, 2009.
Damascelli et al., Intraarterial Chemotherapy with Polyoxyethylated Castor Oil Free Paclitaxel, Incorporated in Albumin Nanoparticles (ABI-007) Phase I Study of Patients with Squamous Cell Carcinoma of the Head and Neck and Anal Canal: Preliminary Evidence of Clinical Activity; 2001 Cancer, vol. 92, No. 10, pp. 2592-2602.
Office Action cited in related U.S. Appl. No. 11/928,278, dated Dec. 28, 2009.
Office Action cited in related U.S. Appl. No. 11/928,250, dated Dec. 29, 2009.
Office Action cited in related U.S. Appl. No. 11/928,289, dated Dec. 30, 2009.
Notice of Reasons for Rejections cited in related Japanese Patent Application No. 2003-577857, dated Mar. 29, 2010.
Office Action cited in related U.S. Appl. No. 11/928,250, dated Aug. 4, 2010.
Office Action cited in related U.S. Appl. No. 11/928,278, dated Aug. 4, 2010.
Office Action cited in related U.S. Appl. No. 11/928,289, dated Aug. 3, 2010.
Office Action cited in related U.S. Appl. No. 10/667,470, dated Jul. 27, 2010.
Josefsson et al., "Suppression of Type II Collagen-Induced Arthritis by the Endogenous Estrogen Metabolite 2-Methoxyestradiol," *Arthritis & Rheumatism*, vol. 40, Issue 1, pp. 154-163 (1997).
Office Action cited in related U.S. Appl. No. 12/870,722, dated Oct. 7, 2010.
Office Action cited in related U.S. Appl. No. 12/870,745, dated Oct. 7, 2010.
Office Action cited in related U.S. Appl. No. 12/076,247, dated Aug. 5, 2010.
Office Action cited in related U.S. Appl. No. 12/320,431, dated Sep. 30, 2010.
Merriam-Webster's Collegiate Dictionary, 10$^{th}$ edition, Merriam-Webster Incorp.: Springfield, MA, 1993, pp. 311.
International Search Report for related International Patent Application No. PCT/US2009/036965, completed Jun. 19, 2009.
Written Opinion of the International Searching Authority for related International Patent Application No. PCT/US2009/036965, completed Jun. 19, 2009.
Notice of Rejections for related Japanese Patent Application No. 2003-577857 completed Jul. 6, 2009, 3 pgs.
Notice of Decision to Grant dated Aug. 30, 2010 cited in related Japanese Patent Application No. 2003-565446.
Canadian Office Action dated Mar. 10, 2010, cited in related Canadian Patent Application No. 2,479,665.
European Search Report for related EP Patent Application No. 10179894, dated Nov. 4, 2010.
Office Action cited in related U.S. Appl. No. 10/697,703, dated Nov. 9, 2010.
Office Action cited in related U.S. Appl. No. 11/367,716, dated Nov. 10, 2010.
Office Action cited in related U.S. Appl. No. 12/117,982, dated Dec. 1, 2010.
Office Action cited in related U.S. Appl. No. 12/292,395, dated Dec. 6, 2010.
Office Action in related U.S. Appl. No. 11/367,716, dated May 19, 2011.
Office Action in related U.S. Appl. No. 11/980,720, dated May 26, 2011.
Office Action in related U.S. Appl. No. 10/677,857, dated Jun. 7, 2011.
Office Action in related U.S. Appl. No. 12/483,188, dated Jun. 23, 2011.
Written Opinion cited in related Singapore Patent Application No. 201006315-4 dated Dec. 2, 2011.
Office Action cited in related U.S. Appl. No. 12/729,018, dated Oct. 14, 2011.
Notice of Reasons for Rejection cited in related Japanese Patent Application No. 2008-227248, dated Oct. 31, 2011.

Canadian Office Action cited in related Canadian Patent Application No. 2,488,499, dated Oct. 17, 2011.
Office Action cited in related U.S. Appl. No. 10/701,064, dated Nov. 14, 2011.
Office Action cited in related U.S. Appl. No. 12/117,982, dated Jul. 8, 2011.
Office Action cited in related U.S. Appl. No. 12/068,706, dated Jul. 20, 2011.
Office Action cited in related U.S. Appl. No. 12/292,091, dated Jan. 18, 2012.
Czeslik et al., "Effect of Temperature on the Conformation of Lysozyme Adsorbed to Silica Particles," *Phys. Chem. Chem. Phys.*, vol. 3, pp. 235-239 (2001).
Abraham, "LXXVII. Some Properties of Egg-White Lysozyme," pp. 622-630 (1939).
Office Action cited in related U.S. Appl. No. 10/619,539, dated Mar. 15, 2011.
Office Action cited in related U.S. Appl. No. 12/870,722, dated Mar. 29, 2011.
Office Action cited in related U.S. Appl. No. 12/870,745, dated Apr. 1, 2011.
Office Action cited in related U.S. Appl. No. 12/076,247, dated Apr. 14, 2011.
Purohit et al., Inhibition of Tumor Necrosis Factor a-Stimulated Aromatase Activity by Microtubule-Stabilizing Agents, Pacilitaxel and 2-Methoxyestradiol, *Biochemical and Biophysical Research Communications*, vol. 261, Issue 1, Jul. 22, 1999, pp. 214-217.
Arsenault et al., Taxol Involution of Collagen-Indued Arthritis: Ultrastructural Correlation with the Inhibition of Synovitis and Neovascularization Clinical Immunology and Immunopathology, vol. 86, Issue 3, Mar. 1998, pp. 280-289.
Office Action cited in related U.S. Appl. No. 12/320,431, dated Apr. 15, 2011.
Office Action cited in related U.S. Appl. No. 11/928,250, dated Apr. 25, 2011.
Office Action cited in related U.S. Appl. No. 11/928,278, dated Apr. 27, 2011.
Office Action cited in related U.S. Appl. No. 12/928,289, dated Apr. 27, 2011.
Office Action cited in related U.S. Appl. No. 10/667,470, dated May 9, 2011.
Office Action in related U.S. Appl. No. 11/980,720, dated Dec. 22, 2010.
European Search Report in related EP Patent Application No. EP 10010944, dated Dec. 13, 2010.
Canadian Office Action in related Canadian Patent Application No. 2475092, dated Jan. 11, 2011.
Calvo et al., "Effect of lysozyme on the stability of polyester nanocapsules and nanoparticles: stabilization approaches," *Biomaterials*, vol. 18, No. 19, pp. 1305-1310 (1997). [Abstract].
Tian et al., Structural Stability Effects on Adsorption of Bacteriophage T4 Lysozyme to Colloidal Silica, *J. Colloid. Interface Sci.*, vol. 200, pp. 146-154 (1998). [Abstract].
Office Action in related U.S. Appl. No. 12/117,982, dated Feb. 2, 2011.
Office Action in related U.S. Appl. No. 10/701,064, dated Feb. 14, 2011.
Canadian Office Action cited in related Canadian Patent Application No. 2488499, dated Dec. 16, 2010.
Office Action in related U.S. Appl. No. 12/292,395, dated May 26, 2010.
Office Action cited in related U.S. Patent Application No. 12/729,018, dated Feb. 23, 2012.
Canadian Office Action cited in related Canadian Application No. 2,492,488, dated Feb. 28, 2012.

* cited by examiner

CONTROLLED-RELEASE NANOPARTICULATE COMPOSITIONS

This application is a continuation-in-part of U.S. patent application Ser. No. 09/164,351, filed on Oct. 1, 1998, now abandoned.

FIELD OF THE INVENTION

The present invention relates to controlled release compositions containing a poorly soluble agent such as a drug. In particular, the present invention relates to compositions in which the poorly soluble agent is present in nanoparticulate form. The present invention also relates to solid oral dosage forms containing such compositions.

BACKGROUND OF THE INVENTION

Controlled release refers to the release of an agent such as a drug from a composition or dosage form in which the agent is released according to a desired profile over an extended period of time. Controlled release profiles include, for example, sustained release, prolonged release, pulsatile release, and delayed release profiles. In contrast to immediate release compositions, controlled release compositions allow delivery of an agent to a subject over an extended period of time according to a predetermined profile. Such release rates can provide therapeutically effective levels of agent for an extended period of time and thereby provide a longer period of pharmacologic or diagnostic response as compared to conventional rapid release dosage forms. Such longer periods of response provide for many inherent benefits that are not achieved with the corresponding short acting, immediate release preparations. For example, in the treatment of chronic pain, controlled release formulations are often highly preferred over conventional short-acting formulations.

Controlled release pharmaceutical compositions and dosage forms are designed to improve the delivery profile of agents, such as drugs, medicaments, active agents, diagnostic agents, or any substance to be internally administered to an animal, including humans. A controlled release composition is typically used to improve the effects of administered substances by optimizing the kinetics of delivery, thereby increasing bioavailability, convenience, and patient compliance, as well as minimizing side effects associated with inappropriate immediate release rates such as a high initial release rate and, if undesired, uneven blood or tissue levels.

The term bioavailability is used to describe the degree to which a drug becomes available at the site(s) of action after administration. The degree and timing in which an agent such as a drug becomes available to the target site(s) after administration is determined by many factors, including the dosage form and various properties, e.g., dissolution rate of the drug. It is well known that some drug compositions suffer from poor bioavailability because of poor solubility of the active ingredient itself.

Numerous methods have been developed for enhancing the bioavailability of poorly soluble drugs. Particle size reduction, such as nanoparticulate forms of the agent, is one such method since the dissolution rate of a compound is related to the particle size. Nanoparticulate compositions comprise poorly water-soluble drug or agent particles having an extremely small particle size, i.e., less than one micron. With a decrease in particle size, and a consequent increase in surface area, a composition tends to be rapidly dissolved and absorbed following administration. For certain formulations, this characteristic can be highly desirable, as described, for example, in U.S. Pat. Nos. 5,145,684, 5,510,118, 5,534,270, and 4,826,689, which are specifically incorporated by reference. However, rapid dissolution is contrary to the goal of controlled release. Known controlled release formulations do not present a solution to this problem.

Prior art teachings of the preparation and use of compositions providing for controlled release of an active compound provide various methods of extending the release of a drug following administration. However, none of the methods suggest a successful method of administering a nanoparticulate formulation.

Exemplary controlled release formulations known in the art include specially coated pellets, microparticles, implants, tablets, minitabs, and capsules in which a controlled release of a drug is brought about, for example, through selective breakdown of the coating of the preparation, through release through the coating, through compounding with a special matrix to affect the release of a drug, or through a combination of these techniques. Some controlled release formulations provide for pulsatile release of a single dose of an active compound at predetermined periods after administration.

U.S. Pat. No. 5,110,605 to Acharya et al. refers to a calcium polycarbophil-alginate controlled release composition. U.S. Pat. No. 5,215,758 to Krishnamurthy et al. refers to a controlled release suppository composition of sodium alginate and calcium salt. U.S. Pat. No. 5,811,388 to Friend et al. refers to a solid alginate-based formulation including alginate, a water-swellable polymer, and a digestible hydrocarbon derivative for providing controlled release of orally administered compounds.

WO 91/13612 refers to the sustained release of pharmaceuticals using compositions in which the drug is complexed with an ion-exchange resin. The specific ion-exchange resin described in this published patent application is AMBERLITE IRP 69®, a sodium polystyrene sulphonate resin.

U.S. Pat. No. 5,811,425 to Woods et al. refers to injectable depot forms of controlled release drugs made by forming microencapsule matrices of the drug in biodegradable polymers, liposomes, or microemulsions compatible with body tissues. U.S. Pat. No. 5,811,422 to Lam et al. refers to controlled release compositions obtained by coupling a class of drugs to biodegradable polymers, such as polylactic acid, polyglycolic acid, copolymers of polylactic and polyglycolic acid, polyepsilon caprolactone, polyhydroxy butyric acid, etc.

U.S. Pat. No. 5,811,404 to De Frees et al. refers to the use of liposomes having prolonged circulation half-lives to provide for the sustained release of drug compositions.

Nanoparticulate compositions addressed a need in the art for pharmaceutically-acceptable compositions containing poorly-water soluble agents. However, the known nanoparticulate compositions are not suitable for controlled-release formulations. There remains a need in the art for controlled release nanoparticulate compositions.

SUMMARY OF THE INVENTION

This invention is directed to the surprising and unexpected discovery of new controlled release nanoparticulate compositions. The controlled release compositions provide for the therapeutically effective release of an incorporated drug or other substance in a patient for a time period ranging from about 2 to about 24 hours or longer.

The controlled release nanoparticulate compositions comprise a nanoparticulate drug or other agent to be administered, such as a crystalline or amorphous nanoparticulate drug or other agent, or a combination of a crystalline and amorphous nanoparticulate drug or other agent, having an effective average particle size, prior to inclusion in the composition, of less than about 1000 nm. The composition also comprises at least one surface stabilizer associated with the surface of the nanoparticulate drug or other agent. In addition, the controlled release nanoparticulate composition comprises one or more pharmaceutically acceptable rate-controlling polymers, which function to prolong release of the administered nanoparticulate drug or agent thereby resulting in controlled release. Optionally, one or more auxilary excipient materials can also be included in the controlled release composition.

Controlled release compositions according to this invention containing a nanoparticulate form of a poorly soluble drug are advantageous in that the improved bioavailability achieved by size reduction of the drug can be exploited to maintain an effective blood concentration over an extended period of time after administration.

Preferably, the effective average particle size of the nanoparticulate agent prior to inclusion in the controlled release nanoparticulate composition is less than about 1000 nm, less than about 800 nm, less than about 600 nm, less than about 400 nm, less than about 300 nm, less than about 250 nm, less than about 100 nm, or less than about 50 nm. Nanoparticulate compositions were first described in U.S. Pat. No. 5,145,684 ("the '684 patent"), described above.

The present invention also provides dosage forms for the controlled release composition as described above in tablet form or in multiparticulate form to be administered in any conventional method, such as via oral, rectal, buccal, and vaginal routes. The tablet form may be, for instance, coated tablets, multilayer tablets, matrix tablets, and the like. The multiparticulate form may be, for instance, particles, pellets, mini-tablets, or the like.

In a first aspect of the invention, the nanoparticulate drug or other agent, at least one surface stabilizer, and one or more auxiliary excipient materials are compressed into tablet form prior to coating with a rate controlling polymer material.

In a second aspect, the nanoparticulate drug or other agent, at least one surface stabilizer, the rate controlling polymer material, and one or more auxiliary excipients are compressed together to form a controlled release matrix. The controlled release matrix may optionally be coated with a rate controlling polymer so as to provide additional controlled release properties.

In a third aspect, the nanoparticulate drug or other agent, at least one surface stabilizer, and one or more auxiliary excipient materials are compressed into the form of a multilayer tablet prior to coating with a rate controlling polymer material.

In a fourth aspect, the nanoparticulate drug or other agent and at least one surface stabilizer are dispersed in the rate controlling polymer material and compressed into the form of a multilayer tablet. The multilayer tablet may optionally be coated with a rate controlling polymer material so as to provide additional controlled release properties. In an alternative aspect, a first layer in such a multilayer tablet comprises a controlled release composition according to the invention and a second layer comprises a conventional active ingredient containing composition, such as an instant release composition.

In a fifth aspect, the nanoparticulate drug or other agent and at least one surface stabilizer are incorporated into a single layer or multilayer tablet containing osmagent surrounded by a semi-permeable membrane, with the semi-permeable membrane defining an orifice. In this embodiment the semi-permeable membrane is permeable to aqueous media, such as gastrointestinal fluids, but it is not permeable to the poorly soluble drug compound when in solution or when in other form. Such osmotic delivery systems are well known in the art, wherein infusion of fluid through the semi-permeable membrane causes the osmagent to swell thus driving the drug compound through the orifice defined by the semi-permeable membrane.

In a sixth aspect, the nanoparticulate drug or other agent, at least one surface stabilizer, one or more auxiliary excipients, and the rate controlling polymer material are combined into a multiparticulate form. The multiparticulate form preferably comprises discrete particles, pellets, mini-tablets, or combinations thereof. In a final oral dosage form the multiparticulate form may be encapsulated, for example in hard or soft gelatin capsules. Alternatively, a multiparticulate form may be incorporated into other final dosage forms such as a sachet. In the case of a multiparticulate form comprising discrete particles or pellets, the multiparticulate form may be compressed, optionally with additional auxiliary excipients, into the form of tablets. The compressed multiparticulate tablet may optionally be coated with rate controlling polymer material so as to provide additional controlled release properties.

The present invention further relates to processes for the manufacture of controlled release compositions in which a poorly soluble drug or other agent is present in nanoparticulate form. In one aspect, the method comprises: (1) forming a nanoparticulate composition comprising a poorly soluble drug or other agent to be administered and a surface stabilizer; (2) adding one or more pharmaceutically acceptable rate-controlling polymers, and (3) forming a solid dose form of the composition for administration. Pharmaceutically acceptable excipients can also be added to the composition for administration. Methods of making nanoparticulate compositions, which can comprise mechanical grinding, precipitation, or any other suitable size reduction process, are known in the art and are described in, for example, the '684 patent.

Yet another aspect of the present invention provides a method of treating a mammal, including a human, requiring extended administration of a drug or other agent with a controlled release nanoparticulate composition of the invention which releases an incorporated drug or other agent providing a desired effect for a period from about 2 to about 24 hours or longer. The controlled release nanoparticulate composition can be administered in any conventional method, such as via oral, rectal, buccal, and vaginal routes.

It is to be understood that both the foregoing general description and the following detailed description are exemplary and explanatory and are intended to provide further explanation of the invention as claimed. Other objects, advantages, and novel features will be readily apparent to those skilled in the art from the following detailed description of the invention.

DETAILED DESCRIPTION OF THE INVENTION

A. Controlled Release Nanoparticulate Compositions

Figure 1:
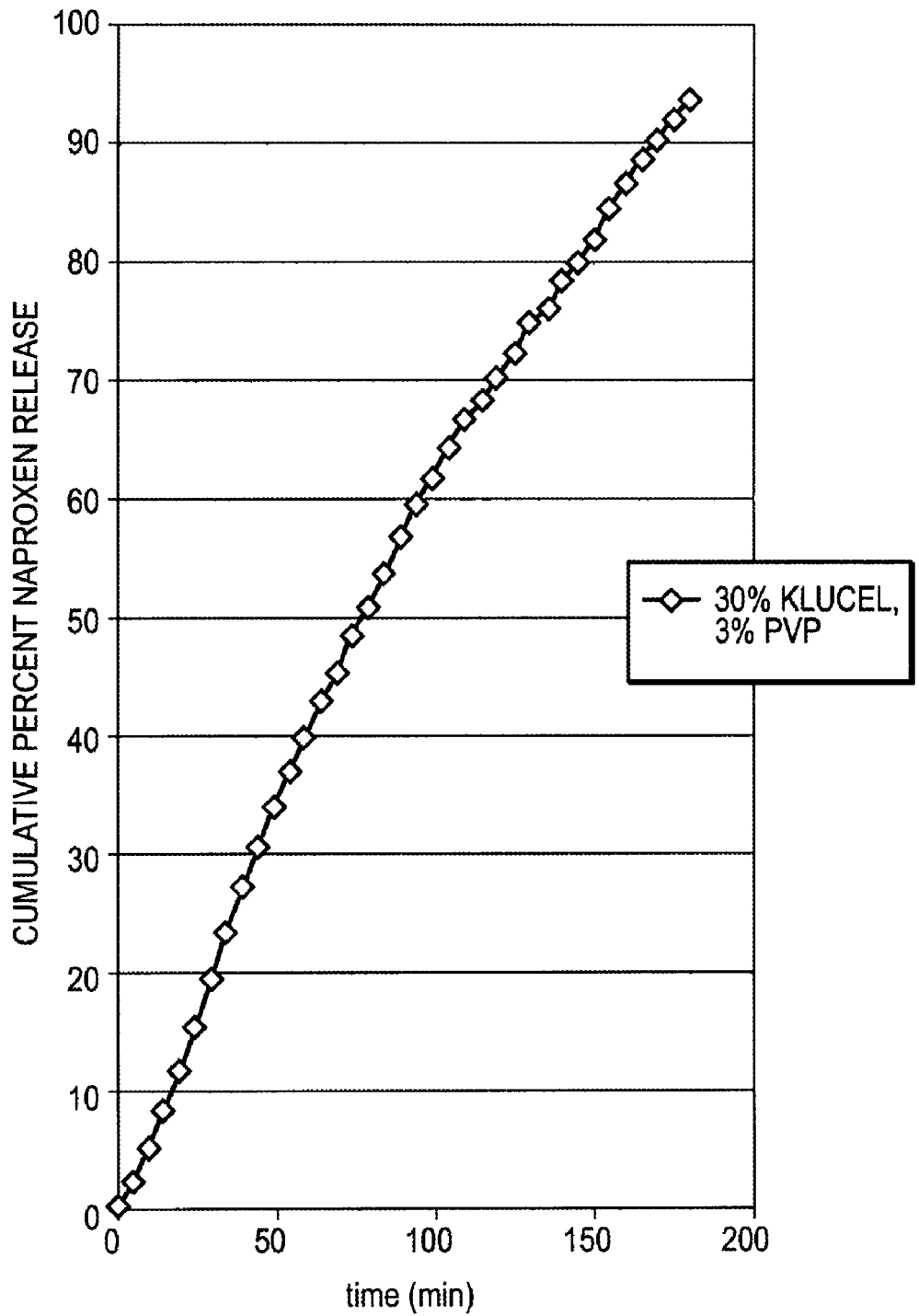
FIG. 1: Shows a graph of the cumulative % drug (naproxen) released over time using a nanoparticulate composition comprising 30% Klucel® hydroxypropylcellulose (HPC) and 3% polyvinylpyrrolidone (PVP)

This invention is directed to the surprising and unexpected discovery of new solid dose controlled release nanoparticulate compositions. It is expected that the controlled release compositions provide effective blood levels of an incorporated nanoparticulate drug or other agent in a patient for an extended period of time. Such a discovery was unexpected because the nanoparticulate size of the drug or other agent, resulting in a large surface area in relation to the volume, results in rapid dissolution of the drug or other agent following administration. Rapid dissolution is seemingly contrary to the goal of controlled release formulations.

As used herein, "controlled release" means the release of an agent such as a drug from a composition or dosage form in which the agent is released according to a desired profile over an extended period of time, such as from about 2 to about 24 hours or longer. Release over a longer time period is also contemplated as a "controlled release" dosage form of the present invention.

The solid dose controlled release nanoparticulate compositions of the invention comprise a crystalline or amorphous nanoparticulate drug or other agent to be administered, having an effective average particle size of less than about 1000 nm, at least one surface stabilizer associated with the surface of the drug or agent, and, additionally, one or more rate-controlling polymers. Preferably, the effective average particle size of the nanoparticulate drug is less than about 800 nm, less than about 600 nm, less than about 400 nm, less than about 300 nm, less than about 250 nm, less than about 100 nm, or less than about 50 nm. The crystalline form of a drug or other agent is distinguishable from a non-crystalline or amorphous phase of a drug or other agent.

1. Nanoparticulate Compositions

The starting nanoparticulate composition (prior to addition of the one or more rate-controlling polymers) comprises a drug or other agent to be administered and at least one surface stabilizer associated with the surface of the nanoparticulate drug or agent.

a. Agent to be Administered

The nanoparticles of the invention comprise a therapeutic agent, diagnostic agent, or other agent to be administered for controlled release. A therapeutic agent can be a drug or pharmaceutical, and a diagnostic agent is typically a contrast agent, such as an x-ray contrast agent, or any other type of diagnostic material. The drug or diagnostic agent exists as a discrete, crystalline phase, as an amorphous phase, or as a combination thereof. The crystalline phase differs from a non-crystalline or amorphous phase that results from precipitation techniques, such as those described in EPO 275,796.

The invention can be practiced with a wide variety of drugs or diagnostic agents. The drug or diagnostic agent is preferably present in an essentially pure form, is poorly water soluble, and is dispersible in at least one liquid medium. By "poorly water soluble" it is meant that the drug or diagnostic agent has a solubility in the liquid dispersion medium of less than about 30 mg/ml, preferably less than about 10 mg/ml, and preferably less than about 1 mg/ml.

Suitable drugs or diagnostic agents include those intended for controlled release delivery. Preferable drug classes include those that have short half-lives for clearance.

The drug can be selected from a variety of known classes of drugs, including, for example, analgesics, anti-inflammatory agents, anthelmintics, anti-arrhythmic agents, antiasthma agents, antibiotics (including penicillins), anticoagulants, antidepressants, antidiabetic agents, antiepileptics, antihistamines, antitussives, antihypertensive agents, antimuscarinic agents, antimycobacterial agents, antineoplastic agents, antipyretics, immunosuppressants, immunostimulants, antithyroid agents, antiviral agents, anxiolytic sedatives (hypnotics and neuroleptics), astringents, beta-adrenoceptor blocking agents, blood products and substitutes, bronchodilators, cardiac inotropic agents, chemotherapeutics, contrast media, corticosteroids, cough suppressants (expectorants and mucolytics), diagnostic agents, diagnostic imaging agents, diuretics, dopaminergics (antiparkinsonian agents), haemostatics, immunological agents, lipid regulating agents, muscle relaxants, proteins, polypeptides, parasympathomimetics, parathyroid calcitonin and biphosphonates, prostaglandins, radio-pharmaceuticals, hormones, sex hormones (including steroids), anti-allergic agents, stimulants and anoretics, sympathomimetics, thyroid agents, vaccines, vasodilators, and xanthines.

A description of these classes of drugs and diagnostic agents and a listing of species within each class can be found, for instance, in Martindale, *The Extra Pharmacopoeia*, Twenty-ninth Edition (The Pharmaceutical Press, London, 1989), specifically incorporated by reference. The drugs or diagnostic agents are commercially available and/or can be prepared by techniques known in the art.

Poorly water soluble drugs which may be suitably used in the practice of the present invention include but are not limited to alprazolam, amiodarone, amlodipine, astemizole, atenolol, azathioprine, azelatine, beclomethasone, budesonide, buprenorphine, butalbital, carbamazepine, carbidopa, cefotaxime, cephalexin, cholestyramine, ciprofloxacin, cisapride, cisplatin, clarithromycin, clonazepam, clozapine, cyclosporin, diazepam, diclofenac sodium, digoxin, dipyridamole, divalproex, dobutamine, doxazosin, enalapril, estradiol, etodolac, etoposide, famotidine, felodipine, fentanyl citrate, fexofenadine, finasteride, fluconazole, flunisolide, flurbiprofen, fluvoxamine, furosemide, glipizide, gliburide, ibuprofen, isosorbide dinitrate, isotretinoin, isradipine, itraconazole, ketoconazole, ketoprofen, lamotrigine, lansoprazole, loperamide, loratadine, lorazepam, lovastatin, medroxyprogesterone, mefenamic acid, methylprednisolone, midazolam, mometasone, nabumetone, naproxen, nicergoline, nifedipine, norfloxacin, omeprazole, paclitaxel, phenytoin, piroxicam, quinapril, ramipril, risperidone, sertraline, simvastatin, terbinafine, terfenadine, triamcinolone, valproic acid, zolpidem, or pharmaceutically acceptable salts of any of the abovementioned drugs.

b. Surface Stabilizers

Useful surface stabilizers, which are known in the art and described, for example, in the '684 patent, are believed to include those which physically adhere to the surface of the drug or agent but do not chemically bond to or interact with the drug or agent. The surface stabilizer is associated with the surface of the drug or agent in an amount sufficient to maintain an effective average particle size of less than about 1000 nm. Furthermore, the individual molecules of the surface stabilizer are essentially free of intermolecular cross-linkages.

Suitable surface stabilizers can preferably be selected from known organic and inorganic pharmaceutical excipients. Such excipients include various polymers, low molecular weight oligomers, natural products, and surfactants. Preferred surface stabilizers include nonionic and ionic surfactants.

Representative examples of surface stabilizers include gelatin, casein, lecithin (phosphatides), dextran, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., the commercially available Tweens20® such as e.g., Tween® and Tween 80® (ICI Specialty Chemicals)); polyethylene glycols (e.g., Carbowaxs 3550® and 934® (Union Carbide)), polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethyl-cellulose phthalate, noncrystalline cellulose, magnesium aluminum silicate, triethanolamine, polyvinyl alcohol (PVA), polyvinylpyrrolidone (PVP), 4-(1,1,3,3-tetramethylbutyl)-phenol polymer with ethylene oxide and formaldehyde (also known as tyloxapol, superione, and triton), poloxamers (e.g., Pluronics F68® and F108®, which are block copolymers of ethylene oxide and propylene oxide); poloxamines (e.g., Tetronic 908®,also known as Poloxamine 908®, which is a tetrafunctional block copolymer derived from sequential addition of propylene oxide and ethylene oxide to ethylenediamine (BASF Wyandotte Corporation, Parsippany, N.J.)); Tetronic 1508® (T-1508) (BASF Wyandotte Corporation), dialkylesters of sodium sulfosuccinic acid (e.g., Aerosol OT®, which is a dioctyl ester of sodium sulfosuccinic acid (American Cyanamid)); Duponol P®, which is a sodium lauryl sulfate (DuPont); Tritons X-200®, which is an alkyl aryl polyether sulfonate (Rohm and Haas); Crodestas F-110®, which is a mixture of sucrose stearate and sucrose distearate (Croda Inc.); p-isononylphenoxypoly-(glycidol), also known as Olin-10G® or Surfactant 10-G® (Olin Chemicals, Stamford, Conn.); Crodestas SL-40® (Croda, Inc.); and SA9OHCO, which is $C_{18}H_{37}CH_2(CON(CH_3)—CH_2(CHOH)_4(CH_2OH)_2$ (Eastman Kodak Co.); decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside; octyl β-D-thioglucopyranoside; and the like.

Most of these surface stabilizers are known pharmaceutical excipients and are described in detail in the *Handbook of Pharmaceutical Excipients,* published jointly by the American Pharmaceutical Association and The Pharmaceutical Society of Great Britain (The Pharmaceutical Press, 1986), specifically incorporated by reference.

c. Particle Size

By "an effective average particle size of less than about 1000 nm" it is meant that at least 50% of the drug/agent particles have an average particle size of less than about 1000 nm when measured by light scattering techniques. Preferably, at least 70% of the particles have an average particle size of less than the effective average, i.e., about 1000 nm, more preferably at least about 90% of the particles have an average particle size of less than the effective average.

As used herein, particle size is determined on the basis of the weight average particle size as measured by conventional particle size measuring techniques well known to those skilled in the art. Such techniques include, for example, sedimentation field flow fractionation, photon correlation spectroscopy, light scattering, and disk centrifugation. By "an effective average particle size of less than about 1000 nm" it is meant that at least 70% of the particles, by weight, have a particle size of less than about 1000 nm when measured by the above-noted techniques. In preferred embodiments, the effective average particle size is less than about 800 nm, less than about 600 nm, less than about 400 nm, less than about 300 nm, less than about 250 nm, less than about 100 nm, or less than about 50 nm.

As used herein, the mean diameter of 50% of the particles, $D_{v,50}$, refers to the volume average diameter of 50% of the particles or the value below which 50% of the particles have an equivalent volume diameter.

2. Rate-controlling Polymers

The present invention identifies pharmaceutically acceptable rate-controlling polymers (also referred to herein as rate controlling polymer material) that unexpectedly provide excellent controlled release properties for nanoparticulate compositions. Rate-controlling polymers include hydrophilic polymers, hydrophobic polymers, and mixtures of hydrophobic and hydrophilic polymers that are capable of retarding the release of a drug compound from a composition or dosage form of the present invention.

Particularly useful rate-controlling polymers for causing an effective controlled release of administered drug or agent following administration include plant exudates (gum arabic), seaweed extracts (agar), plant seed gums or mucilages (guar gum), cereal gums (starches), fermentation gums (dextran), animal products (gelatin), hydroxyalkyl celluloses such as hydroxypropyl cellulose (HPC), hydroxyethyl cellulose (HEC), hydroxypropyl methylcelluose (HPMC), and sodium carboxymethylcellulose (CMC), guar, pectin, and carrageenan. Additional polymers include poly(ethylene) oxide, alkyl cellulose such as ethyl cellulose and methyl cellulose, carboxymethyl cellulose, hydrophilic cellulose derivatives, polyethylene glycol, polyvinylpyrrolidone, cellulose acetate, cellulose acetate butyrate, cellulose acetate phthalate, cellulose acetate trimellitate, polyvinyl acetate phthalate, hydroxypropylmethyl cellulose phthalate, hydroxypropylmethyl cellulose acetate succinate, polyvinyl acetaldiethylamino acetate, poly(alkylmethacrylate) and poly(vinyl acetate). Other suitable hydrophobic polymers include polymers and/or copolymers derived from acrylic or methacrylic acid and their respective esters, waxes, shellac, and hydrogenated vegetable oils. Two or more rate-controlling polymers can be used in combination. The polymers are commercially available and/or can be prepared by techniques known in the art.

3. Other Pharmaceutical Excipients

Pharmaceutical compositions according to the invention may also comprise one or more auxiliary excipients such as binding agents, diluents, lubricating agents, plasticisers, antitack agent, opacifying agents, suspending agents, sweeteners, flavoring agents, preservatives, buffers, wetting agents, disintegrants, pigments, and other excipients. Such excipients are known in the art. As will be appreciated by those skilled in the art, the exact choice of excipients and their relative amounts will depend to some extent on the dosage form into which the controlled release composition is incorporated.

Suitable diluents include for example pharmaceutically acceptable inert fillers such as microcrystalline cellulose, lactose, dibasic calcium phosphate, saccharides, and/or mixtures of any of the foregoing. Examples of diluents include microcrystalline cellulose such as Avicel pH101, Avicel pH102, and Avicel pH112; lactose such as lactose monohydrate, lactose anhydrous, and Pharmatose DCL21; dibasic calcium phosphate such as Emcompress; mannitol; starch; sorbitol; sucrose; and glucose. The diluent, if present, is preferably used in an amount of from about 5 mg to about 800 mg per dosage unit, more preferably from about 10 mg to about 600 mg per dosage unit and most preferably from about 20 mg to about 400 mg per dosage unit.

Examples of binding agents are various celluloses and cross-linked polyvinylpyrrolidone.

Suitable lubricants, including agents that act on the flowability of the powder to be compressed, are colloidal silicon dioxide, such as Aerosil 200; talc, stearic acid, magnesium stearate, calcium stearate, stearic acid, and silica gel.

Examples of sweeteners are any natural or artificial sweetener, such as sucrose, xylitol, sodium saccharin, cyclamate, aspartame, and acsulfame. Examples of flavoring agents are Magnasweet (trademark of MAFCO), bubble gum flavor, and fruit flavors, and the like.

Examples of preservatives are potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quarternary compounds such as benzalkonium chloride.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

4. Quantities of Nanoparticulate Composition and Rate-controlling Polymer(s)

The relative amount of nanoparticulate agent in the controlled release compositions of the invention can vary widely and can depend upon, for example, the agent selected for controlled release delivery. The poorly soluble drug or pharmaceutically acceptable salt thereof may be present in any amount which is sufficient to elicit a therapeutic effect and, where applicable, may be present either substantially in the form of one optically pure enantiomer or as a mixture, racemic or otherwise, of enantiomers. The amount of poorly soluble drug compound, or pharmaceutically acceptable salt thereof, in the controlled release composition of the present invention is suitably in the range of from about 1 μg to about 800 mg, preferably in the range of from about 0.25 mg to about 600 mg and more preferably in the range of from about 1 mg to about 500 mg.

The nanoparticulate agent, preferably in combination with the surface stabilizer, can be present in the controlled release compositions of the invention in an amount of about 95% to about 5%, preferably about 80% to about 10% by weight based on the total weight of the dry composition.

The one or more rate-controlling polymers can be present in an amount of about 5% to about 95%, preferably about 10% to about 65% by weight based on the total weight of the dry composition.

5. Optimization of Other Variables for Increasing Controlled Release

Other than selection of the one or more rate-controlling polymers, hardness of the tablet is the factor which contributes most to extended controlled release of the administered agent. A hardness of about 10 kP to about 50 kP is preferred, with a hardness of about 30 to about 35 kP being most preferred. Factors such as wet-granulation of the rate-controlling polymer and an increase in the concentration of the rate-controlling polymer allow for a more controlled release, while factors such as micronization of the rate-controlling polymer give a more immediate release of the administered agent.

B. Methods of Making Controlled Release Nanoparticulate Dosage Forms

In another aspect of the invention there is provided a method of preparing controlled release nanoparticulate formulations. The method comprises: (1) forming a nanoparticulate composition comprising an agent to be administered and, preferably, a surface stabilizer; (2) adding one or more rate-controlling polymers, and (3) forming a solid dose form of the composition for administration. Pharmaceutically acceptable excipients can also be added to the composition for administration. Methods of making nanoparticulate compositions, which can comprise mechanical grinding, precipitation, or any other suitable size reduction process, are known in the art and are described in, for example, the '684 patent. A redispersing agent or combination of redispersing agents may be included to facilitate processing of the nanoparticulate drug.

Methods for making solid dose pharmaceutical formulations are known in the art, and such methods can be employed in the present invention. Exemplary solid dose controlled release formulations of the invention can be prepared by, for example, combining the one or more rate-controlling polymers with a raw nanoparticulate mixture obtained after size reduction of an agent to be administered. The resultant composition can be formulated into tablets for oral administration. Alternatively, the one or more rate-controlling polymers can be combined with a nanoparticulate dispersion that has been spray dried.

Oral dosage forms of the controlled release composition according to the present invention can be in the form of tablets or can be multiparticulate. The term "tablet" or "tablets" as used herein includes, but is not limited to, instant release (IR) tablets, matrix tablets, multilayer tablets, and multilayer matrix tablets which may be optionally coated with one or more coating materials. The term "tablet" also includes osmotic delivery systems in which a drug compound is combined with an osmagent (and optionally other excipients) and coated with a semi-permeable membrane, the semi-permeable membrane defining an orifice through which the drug compound may be released. Tablet oral dosage forms particularly useful in the practice of the invention include those selected from the group consisting of coated IR tablets, matrix tablets, coated matrix tablets, multilayer tablets, coated multilayer tablets, multilayer matrix tablets, and coated multilayer matrix tablets. The term "multiparticulate" as used herein includes discrete particles, pellets, mini-tablets, and mixtures or combinations thereof. If the oral form is a multiparticulate capsule, such hard or soft gelatin capsules can suitably be used to contain the multiparticulate. A multiparticulate oral dosage form according to the invention may comprise a blend of two or more populations of particles, pellets, or mini-tablets having different in vitro and/or in vivo release characteristics. For example, a multiparticulate oral dosage form may comprise a blend of an instant release component and a delayed release component contained in a suitable capsule.

If desired, the multiparticulate may be coated with a layer containing controlled release polymer material. Alternatively, the multiparticulate and one or more auxiliary excipient materials can be compressed into tablet form such as a multilayer tablet. Typically, a multilayer tablet may comprise two layers containing the same or different levels of the same active ingredient having the same or different release characteristics. Alternatively, a multilayer tablet may contain different active ingredient in each layer. Multilayer tablets may optionally be coated with a controlled release polymer so as to provide additional controlled release properties.

In one embodiment of the invention the rate controlling polymer material is applied as a coating to tablets comprising the poorly soluble drug compound and any auxiliary excipients which may be required. The coating may be applied to the tablets by any suitable technique. Such techniques will be apparent to those skilled in the art. Particularly useful for application of the coating is the technique of spray coating, carried out for instance using a fluidised bed coating apparatus or using a side vented coating pan. Suitable auxiliary excipients and/or additives may be added to the coating formulation. For example, it may be desirable to add plasticisers, glidants, anti-tack agents, pigments, and other excipients to the coating formulation. The coating may be applied to the tablets in any amount which is sufficient to give the desired degree of controlled release.

In one embodiment a process for the manufacture of a controlled release composition comprises the steps of: (i) spray drying a nanoparticulate dispersion of a poorly soluble drug, optionally in the presence of a surfactant or a surface stabilizer, to form a redispersible material; (ii) blending the redispersible material with auxiliary excipients to form a blend, (iii) compressing the blend into tablets, and (iv) coating the tablets with a rate controlling polymer material.

In an another embodiment, a process for the manufacture of a controlled release composition comprises the steps of: (i) spray drying a nanoparticulate dispersion of a poorly soluble drug, optionally in the presence of a surfactant or a surface stabilizer, to form a redispersible material; (ii) blending the redispersible material with a rate controlling polymer material and optionally auxiliary excipients to form a blend, and (iii) compressing the blend to form tablets. The process may optionally comprise the additional step of coating the tablets with an additional rate controlling polymer material.

1. Spray Drying of Nanoparticulate Dispersions

Solid dose forms of nanoparticulate dispersions can be prepared by drying the nanoparticulate formulation following size reduction. A preferred drying method is spray drying. The spray drying process is used to obtain a nanoparticulate powder following the size reduction process used to transform the drug into nanoparticulate sized particles. Such a nanoparticulate powder can be formulated into tablets for oral administration.

In an exemplary spray drying process, the nanoparticulate drug suspension is fed to an atomizer using a peristaltic pump and atomized into a fine spray of droplets. The spray is contacted with hot air in the drying chamber resulting in the evaporation of moisture from the droplets. The resulting spray is passed into a cyclone where the powder is separated and collected. The spray dryer can be assembled in a co-current configuration with a rotary atomization nozzle and the nanosuspension can be fed to the rotary atomizer using a peristaltic pump.

2. Tableting

The controlled release nanoparticulate formulations of the invention can be in the form of tablets for oral administration. Preparation of such tablets can be by pharmaceutical compression or molding techniques known in the art. The tablets of the invention may take any appropriate shape, such as discoid, round, oval, oblong, cylindrical, triangular, hexagonal, and the like.

The tablets may be coated or uncoated. If coated they may be sugar-coated (to cover objectionable tastes or odors and to protect against oxidation), film coated (a thin film of water soluble matter for similar purposes), or enteric coated (to resist dissolution in gastric fluid but allow disintegration of the coating in the small intestine).

Tableting techniques known to one of ordinary skill in the art are described in, for example, the 18th edition of *Remington's Pharmaceutical Sciences,* Chapter 89, pp. 1633-1658 (Mach Publishing Company, 1990), which is specifically incorporated by reference. In the simplest procedure, the ingredients (except for any lubricant) are blended together to provide a mixture having the active ingredient uniformly dispersed throughout. A lubricant can then be added and blended, and the tablets are compressed using an appropriate tableting machine.

Formulations suitable for tableting are prepared using, for example, a V-blender (Blend Master Lab Blender, Patterson Kelley Co.). In an exemplary method, the nanoparticulate composition and the one or more rate-controlling polymers are added to the V-blender and blended periodically, followed by the addition of other excipients, such as lactose, magnesium stearate, or PVP, followed by periodic blending in the V-Blender.

Tableting can be accomplished by using, for example, a Carver Press (Carver Laboratory Equipment). In such a method, the correct amount of material is loaded into the punches, followed by pressing together at the appropriate pressure and time interval, and removal of the formed tablet.

Yet another exemplary method for creating tablets is wet-granulation. Wet-granulation comprises mixing water and/or granulating fluid to the dry materials (nanoparticulate composition (comprising a drug and surface stabilizer), rate-controlling polymer, and any additives). After thorough granulation, the material is sieved through a coarse mesh screen and dried. The material is then re-sieved through a fine mesh screen and blended with, for example, magnesium stearate, followed by tableting to create tablets.

Tablets are tested to determine that they meet the correct hardness specifications. An exemplary tablet hardness tester is an Erweka TBH 30 (Erweka Instruments, Inc.).

C. Administration of Controlled Release Nanoparticulate Compositions or Dosage Forms Yet another aspect of the present invention provides a method of treating a mammal, including a human, requiring extended administration of a drug or other agent. The administered controlled release nanoparticulate composition releases an incorporated drug or other agent over a prolonged period of time providing a desired effect for a period from about 2 to about 24 hours or more.

In general, the compositions of the invention will be administered to a mammalian subject in need thereof using a level of drug or agent that is sufficient to provide the desired physiological effect via any conventional method, such as orally, rectally, buccally, or via the vagina. The mammalian subject may be a domestic animal or pet but preferably is a human subject. The level of drug or agent needed to give the desired physiological result is readily determined by one of ordinary skill in the art by referring to standard texts, such as *Goodman and Gillman* and the *Physician's Desk Reference*.

The following examples are given to illustrate the present invention. It should be understood, however, that the invention is not to be limited to the specific conditions or details described in these examples. Throughout the specification, any and all references to a publicly available documents are specifically incorporated into this patent application by reference.

EXAMPLE 1

The purpose of this experiment was to demonstrate a reasonable amount of controlled release with a nanoparticulate drug formulation.

29% w/w spray-dried nanoparticulate naproxen intermediate (SDI) (containing 93% w/w nanoparticulate naproxen and 7% w/w polyvinylpyrrolidone (PVP) as a surface stabilizer (sieve #20)), 30% w/w Klucel® HPC polymer (sieve #40), 40% w/w lactose (Foremost #316 Fast-fib, sieve #40), and 1% w/w magnesium stearate (Spectrum, sieve #40) were combined as follows to form a controlled release nanoparticulate formulation tablet to be tested.

The average effective particle size of the nanoparticulate naproxen prior to spray-drying to form spray-dried nanoparticulate naproxen intermediate was 226 nm, with 90% of the particles having a size of less than 297 nm. The spray-dried powder had a mean particle size of about 26 μm. This particle size information for the naproxen SDI is applicable to the following Examples 2-10.

(The sources given in this example for the naproxen SDI, PVP, Klucel® (an HPC polymer), lactose, and magnesium stearate are also applicable to the following examples.)

The naproxen SDI and Klucel® were added to a V-blender (Blend Master Lab Blender, Patterson Kelley Co.) and blended for 10 min. The lactose was then added to the blender and blended for 10 min. Finally, the magnesium stearate was added to the blender and blended for 3 min.

This material was formed into tablets using a Carver Press (Carver Laboratory equipment, model #3912). The resultant tablets had a weight of 500 mg and a hardness of about 9 to about 12 kP Testing for Controlled Release A Distek Dissolution System (used with the Hewlett Packard Diode Array Spectrophotometer 8452A and the Hewlett Packard Flow Control device model 89092A) was used in testing for controlled release. The temperature (37° C.) and agitation of this instrument simulates the body system as it attempts to dissolve the drug in the tablet.

A phosphate buffer at pH 7.4 is used for the testing medium, prepared as follows: 230.0 grams of sodium phosphate dibasic, anhydrous (J. T. Baker) plus 52.4 grams of sodium phosphate monobasic, dihydrate (J. T. Baker) added to 20.0 liters of deionized water and stirred at 2300 rpm for two hours.

Phosphate buffer (900 ml) and a tablet were placed into a container of the Distek System at 37° C. The tablets were agitated, resulting in dissolution of the tablets within a range of 40-50 min. Such a time period is not suitable for controlled release applications.

EXAMPLE 2

The purpose of this experiment was to demonstrate controlled release with a nanoparticulate drug formulation.

To improve the controlled release characteristics of the formed tablets, (i) the weight of the tablet was increased from 500 to 750 mg, (ii) the hardness of the tablet was increased from 9-12 to 35-37 kP; and (iii) 3% extra PVP was added as a binder agent in place of 3% lactose.

Naproxen SDI (containing 93% w/w nanoparticulate naproxen and 7% w/w PVP), 30% w/w Klucel® and 3% w/w PVP (Plasdone K-90 (Povidone USP), ISP Technologies) were combined as in Example 1 to form a tablet of 750 mg with a hardness of 35-37 kP (the PVP was added after addition of the lactose and blended for 5 additional min. in the V-Blender prior to tableting). Quantities of each component in the tablet are given below (mg).

| Naproxen SDI | Klucel ® | Lactose | PVP | Mg Stearate |
|---|---|---|---|---|
| 217.5 | 225 | 277.5 | 22.5 | 7.5 |

Following testing with the Distek Dissolution System, the results demonstrated a steady controlled release of drug over a three hour time period, as shown in FIG. 1.

EXAMPLE 3

The purpose of this experiment was to determine the effects of the hardness of a tablet on controlled release of the nanoparticulate agent.

Three separate hardnesses were tested simultaneously: 15 kP, 25 kP, and 35 kP. Tablets were made as in Example 1, comprising 29% naproxen SDI, 30% Klucel®, and 3% PVP. Quantities of each component in each of the tablet formulations are given below (mg).

| Hardness | Naproxen SDI | Klucel ® | Lactose | PVP | Mg Stearate |
|---|---|---|---|---|---|
| 15 | 217.5 | 225 | 277.5 | 22.5 | 7.5 |
| 25 | 217.5 | 225 | 277.5 | 22.5 | 7.5 |
| 35 | 217.5 | 225 | 277.5 | 22.5 | 7.5 |

Figure 2:
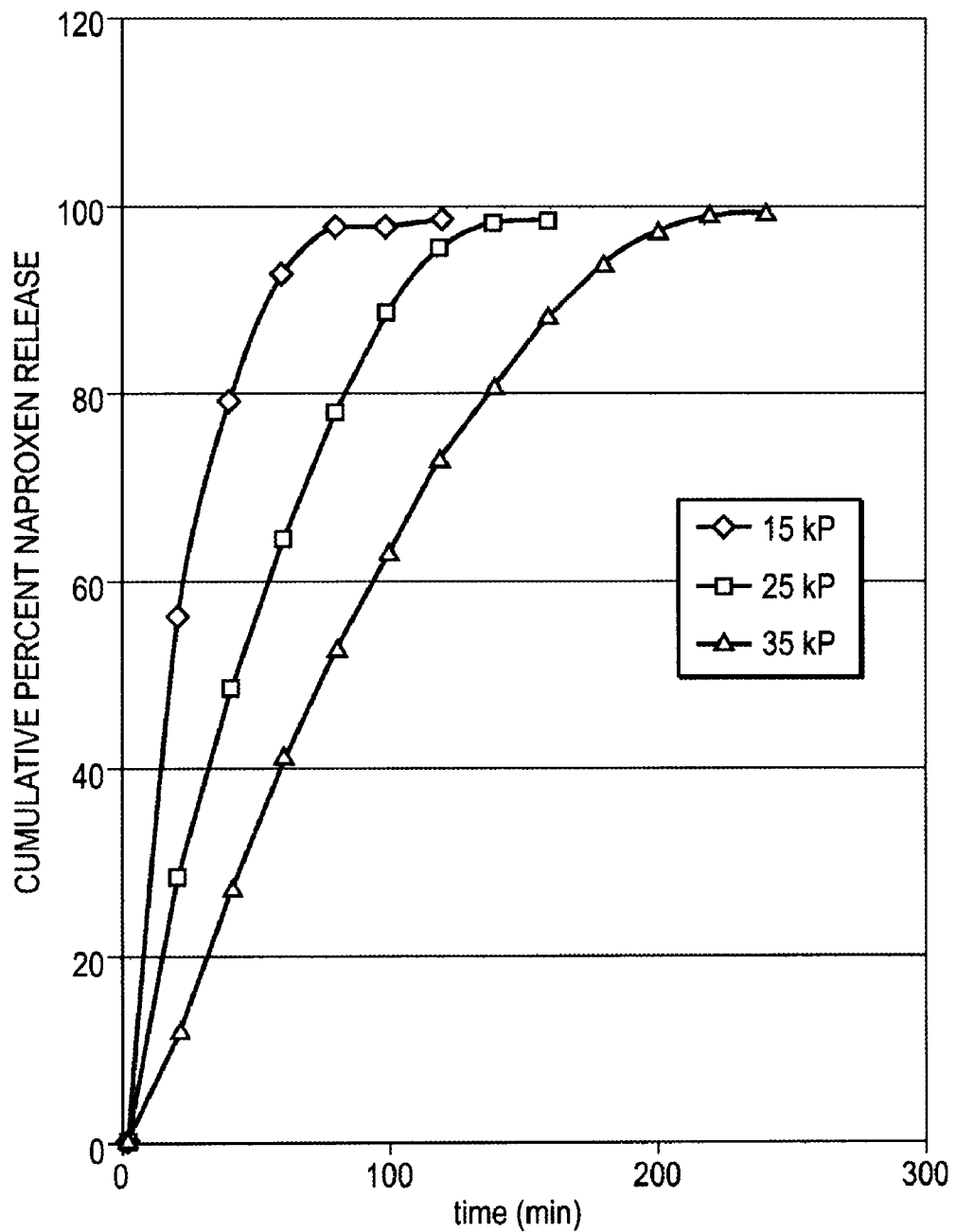
FIG. 2: Shows a graph of the cumulative % drug (naproxen) released over time for three different nanoparticulate compositions having a hardness of 15, 25, and 35 kP.

The results shown in FIG. 2 demonstrate that as the hardness of a tablet increases, the controlled release characteristics of the tablet also steadily increase. Tablets having a hardness of about 15 kP, 25 kP, and 35 kP released naproxen for about 65 min., 140 min., and 240 min., respectively, showing a direct correlation between tablet hardness and increased controlled release of the administered agent.

EXAMPLE 4

The purpose of this experiment was to compare the controlled release characteristics of two different rate-controlling polymers: Klucel® HPC and Shinetzu® L-HPC.

Tablets were made as in Example 1, with 20% Klucel® HPC (without the 3% PVP K-90) and with 20% Shinetzu® L-HPC. Quantities of each component in each of the tablet formulations are given below (mg).

| Naproxen SDI | Klucel ® HPC | Shinetzu ® L-HPC | Lactose | Mg Stearate |
|---|---|---|---|---|
| 292.5 | 150 | 0 | 300 | 7.5 |
| 292.5 | 0 | 150 | 300 | 7.5 |

Figure 3:
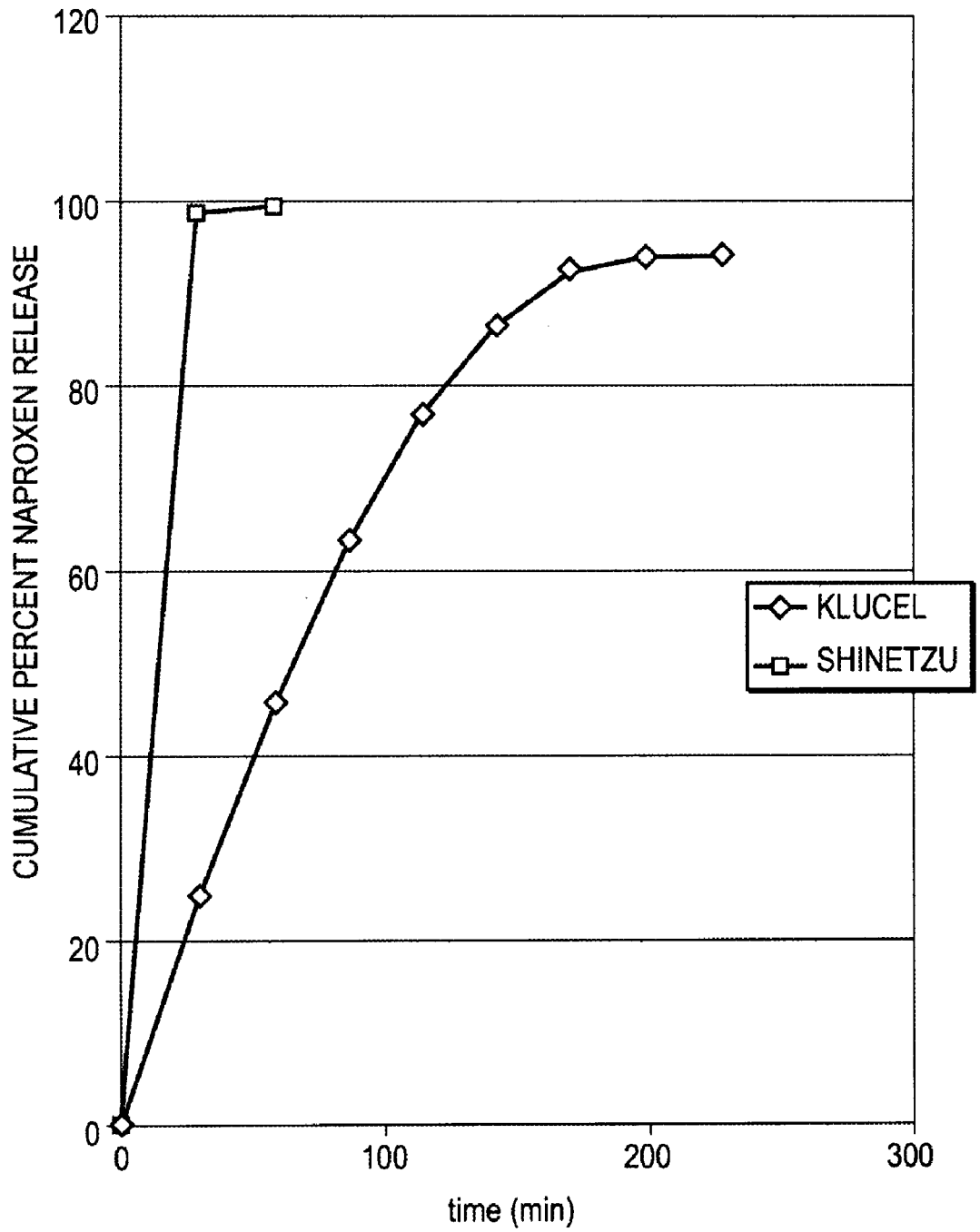
FIG. 3: Shows a graph of the cumulative % drug (naproxen) released over time for nanoparticulate compositions comprising different types of hydroxypropyl methylcellulose (HPMC)

The resultant tablets had a hardness of 35 kP. The results, shown in FIG. 3, demonstrate that the tablet with 20% Klucel® as the polymer completely released within three to four hours, and the tablet with 20% Shinetzu® L-HPC as the polymer allowed the tablet to dissolve in only one hour.

EXAMPLE 5

The purpose of this experiment was to compare the controlled release characteristics of different grades of Methocel® hydroxypropyl methyl cellulose (HPMC) used as the rate-controlling polymer: (i) Methocel® K4M, (ii) Methocel® E4M, (iii) Methocel® K15M, (iv) Methocel® K100LV, (v) Methocel® K100LV, and (vi) Methocel® E10M.

Tablets were prepared as in Example 1, using a 20% concentration of Methocel® HPMC. Quantities of each component in each of the tablet formulations are given below (mg).

| Naproxen SDI | Methocel ® HPMC | Lactose | Mg Stearate |
|---|---|---|---|
| 292.5 | 150 (K4M) | 300 | 7.5 |
| 292.5 | 150 (E4M) | 300 | 7.5 |
| 292.5 | 150 (K15M) | 300 | 7.5 |
| 292.5 | 150 (K100LV) | 300 | 7.5 |
| 292.5 | 150 (K100LV) | 300 | 7.5 |
| 292.5 | 150 HPMC E10M | 300 | 7.5 |

Figure 4:
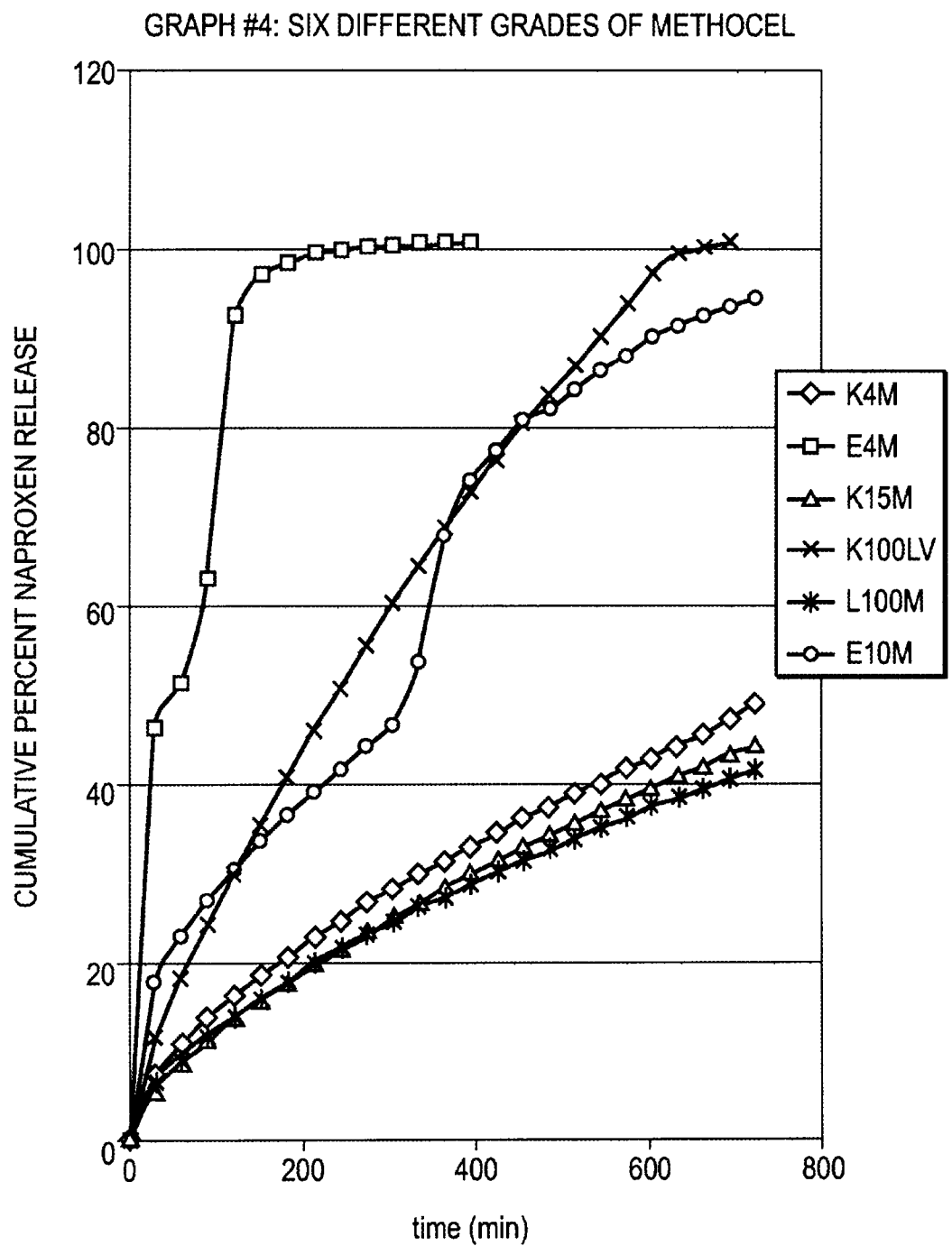
FIG. 4: Shows a graph of the cumulative % drug (naproxen) released over time for nanoparticulate compositions comprising one of six different types of HPMC.

The tablets had a hardness of about 35 to about 37 kP. Each of the Methocel® grades tested in the Distek Dissolution system, was found to exert some extent of controlled release on the nanoparticulate formulation, as shown in FIG. 4. Methocel® grades K4M, K15 M, and K100M gave an extreme amount of controlled release (40-50% in 12 hours), Methocel® grade E4M dissolved in only about three hours, and Methocel® grades K100LV and E10M gave a release over about 12 to about 14 hours.

EXAMPLE 6

The purpose of this example was to determine the effect of adding hydrogenated vegetable oil (Lubritab®) to controlled release of a nanoparticulate agent.

Tablets were prepared as in Example 1, with 30% Klucel® used as the rate-controlling polymer. 3% Lubritab® (Mendel, a Penwest Company) was used in the tablets. The tablets had a hardness of 20-22 kP. Quantities of each component in each of the tablet formulations are given below (mg).

| Naproxen SDI | Klucel ® | Lactose | Lubritab ® | Mg. Stearate |
|---|---|---|---|---|
| 217.5 | 225 | 300 | 0 | 7.5 |
| 217.5 | 225 | 262.5 | 37.5 | 7.5 |
| 217.5 | 225 | 225 | 75 | 7.5 |
| 217.5 | 225 | 150 | 150 | 7.5 |

Figure 5:
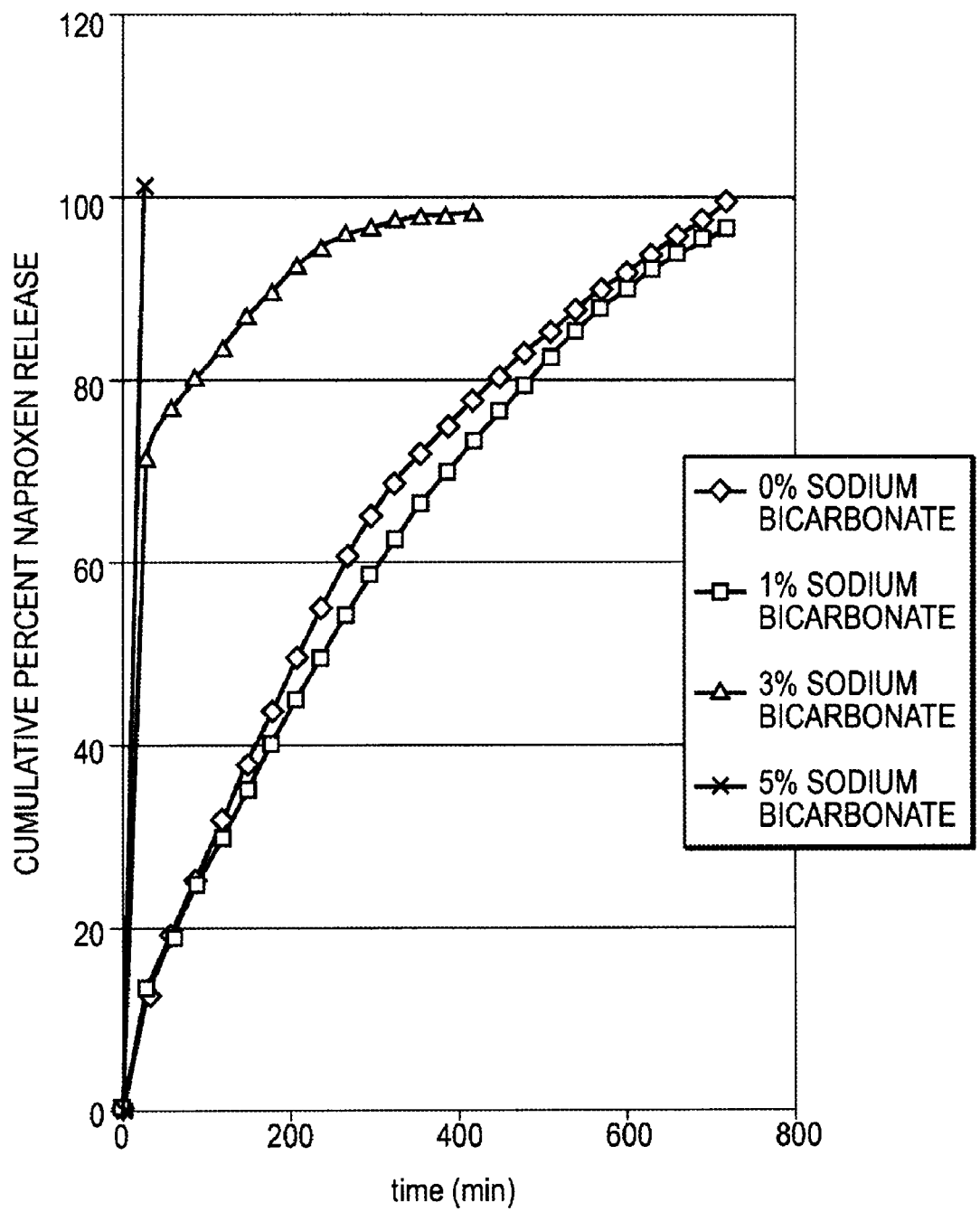
FIG. 5: Shows a graph of the cumulative % drug (naproxen) released over time for nanoparticulate compositions having varying amounts Lubritab® (a hydrogenated vegetable oil)

As shown in FIG. 5, the addition of Lubritab® to a nanoparticulate formulation can allow for an increase in controlled release of the administered agent. While the composition containing 0% Lubritab® was completely released at about 60 min., the composition containing 20% Lubritab® was released over about 175 min.

EXAMPLE 7

The purpose of this example was to compare the controlled release properties of a composition of a spray-dried nanoparticulate formulation mixed with a rate-controlling polymer and a powder composition of unmilled naproxen and surface stabilizer blended with a rate-controlling polymer.

Tablets were prepared as in Example 1. The concentration of the administered agent (naproxen) and surface stabilizer, PVP, was the same for both compositions: 93% naproxen and 7% PVP. The rate-controlling polymer used was Methocel® K100LV in a concentration of 20%. Quantities of each component in each of the tablet formulations are given below (mg).

| Naproxen SDI | Naproxen + PVP | Methocel ® K100LV | Lactose | Mg Stearate |
|---|---|---|---|---|
| 292.5 | 0 | 150 | 300 | 7.5 |
| 0 | 292.5 | 150 | 300 | 7.5 |

Figure 6:
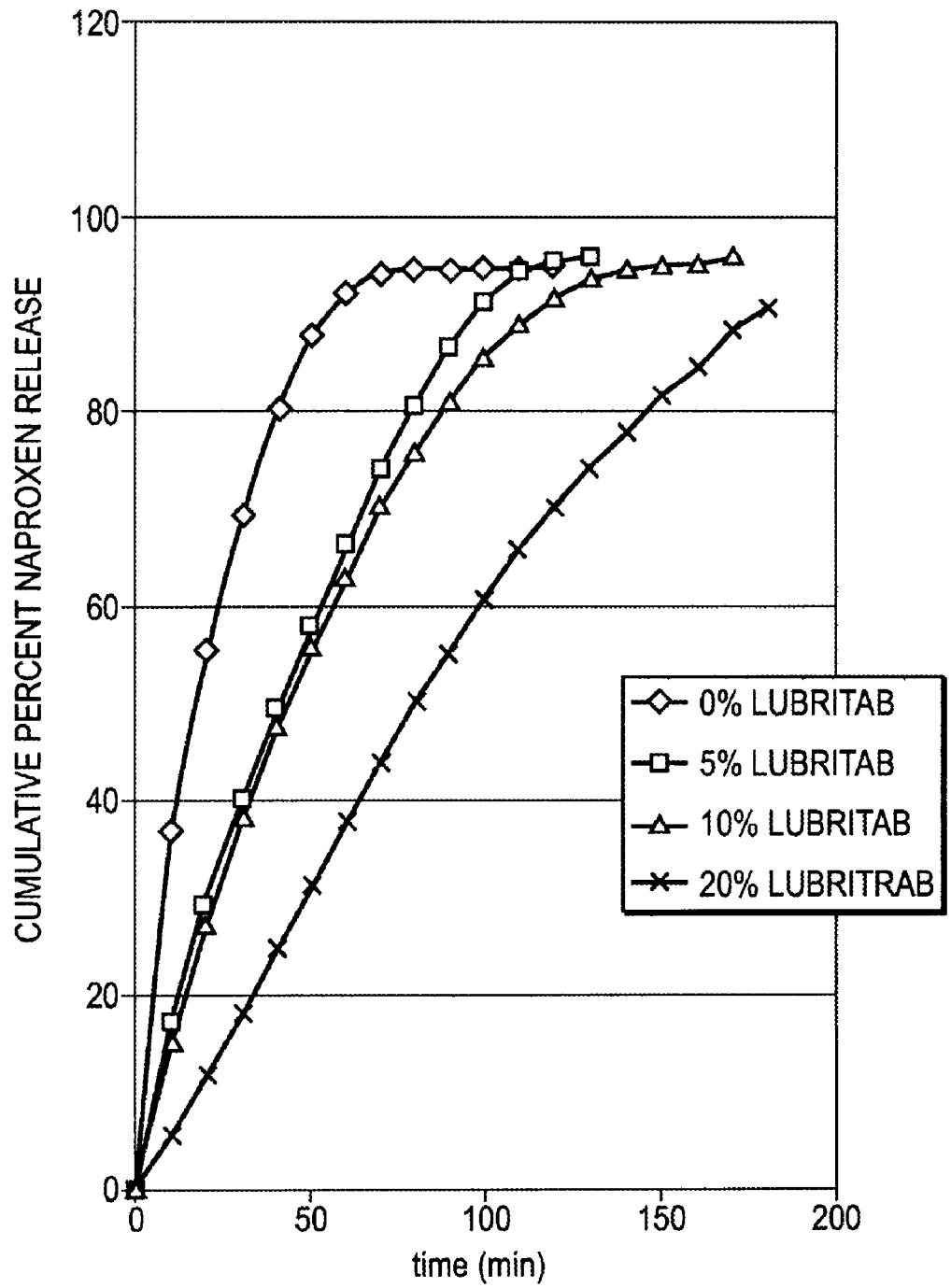
FIG. 6: Shows a graph comparing the cumulative % drug (naproxen) released over time for a spray-dried nanoparticulate formulation and a formulation of blended raw drug and stabilizer.

The tablets had a hardness of 30 kP. As shown in FIG. 6, the composition of raw drug and surface stabilizer blended with a rate-controlling polymer had a more prolonged release as compared to the composition of the spray-dried nanoparticulate formulation mixed with a rate-controlling polymer. The results indicate that complete release of the composition of raw drug and stabilizer blended with a rate-controlling polymer occurred after about 10 hours, while complete release of the spray-dried nanoparticulate formulation mixed with a rate-controlling polymer was expected to occur after about 13 to about 14 hours (complete release of the latter composition had not occurred after 12 hours, when the results were analyzed).

EXAMPLE 8

The purpose of this example was to determine the effect of rate-controlling polymer concentration on the controlled release characteristics of nanoparticulate formulations.

The first test determined the controlled release characteristics of a nanoparticulate formulation comprising 5% Methocel® K100LV, and the second test determined the controlled release characteristics of a nanoparticulate formulation comprising 10% Methocel® K100LV. Controlled release characteristics of a nanoparticulate formulation comprising 20% Methocel® K100LV were obtained in Example 9 (FIG. 6) and are repeated here.

Tablets were prepared as in Example 1, with quantities of each component in each of the tablet formulations are given below (mg).

| Naproxen SDI | Methocel ® K100LV | Lactose | Mg Stearate |
|---|---|---|---|
| 405 | 37.5 | 300 | 7.5 |
| 367.5 | 75 | 300 | 7.5 |
| 292.5 | 150 | 300 | 7.5 |

Figure 7:
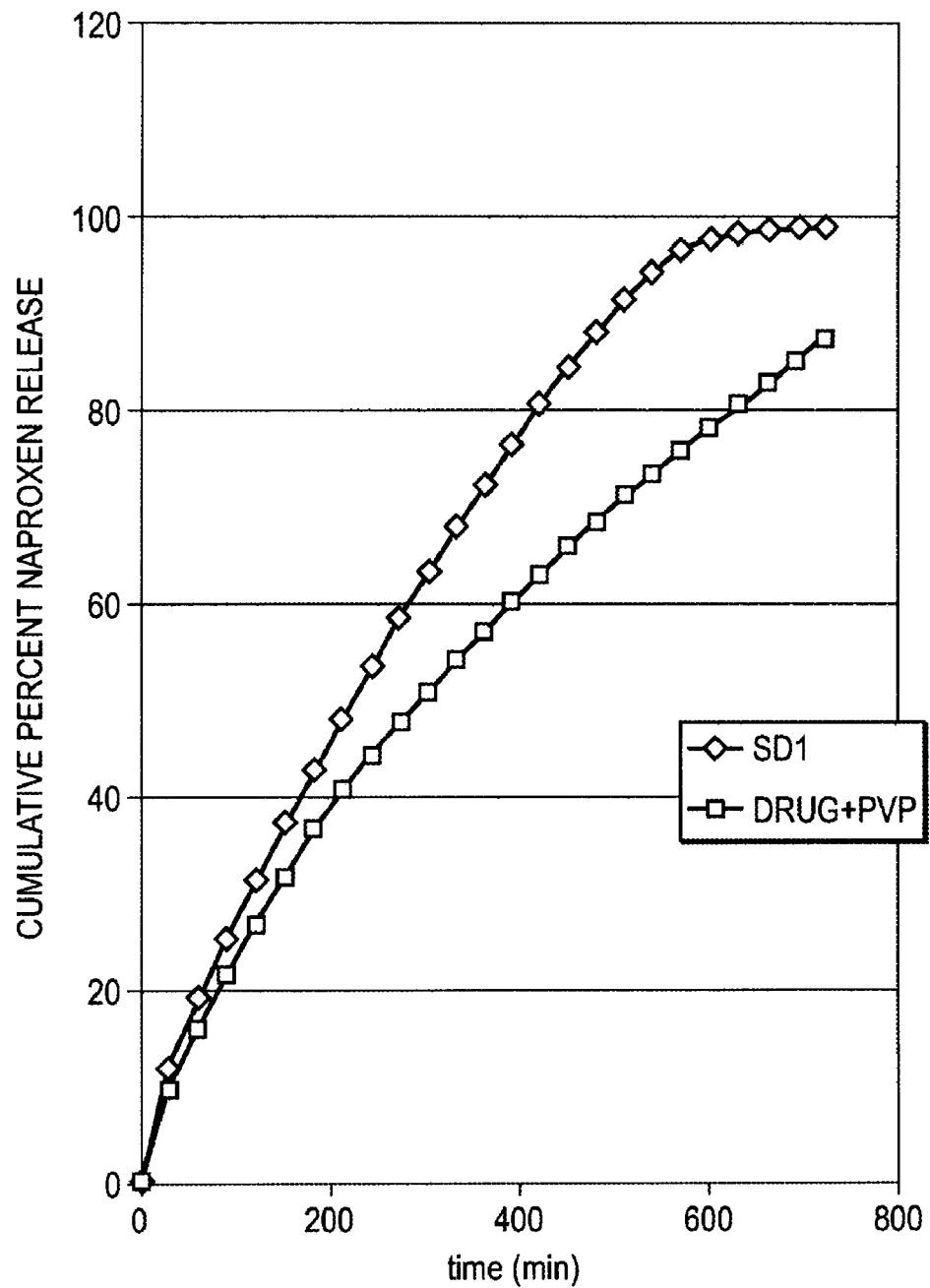
FIG. 7: Shows a graph comparing the cumulative % drug (naproxen) released over time for nanoparticulate formulations comprising different concentrations of Methocel® KlOOLV (HPMC)

The results, shown in FIG. 7, show that with tablets having an identical hardness and varying rate-controlling polymer concentrations, the tablet having the greatest rate-controlling polymer concentration will have the most prolonged drug release characteristics. The tablet having a 5% polymer concentration completely released after about 50 min.; the tablet having a 10% polymer concentration completely released after about 350 min.; and the tablet having a 20% polymer concentration completely released after about 650 min. Thus, increased polymer concentration in the nanoparticulate formulation is directly correlated with prolonged release of the administered agent.

EXAMPLE 9

The purpose of this example was to determine the effect of wet granulation on controlled release of nanoparticulate formulations.

Tablets were formed as in Example 1, except that a small amount of water was added into each mixture to form granules. The granules were then sieved through a coarse mesh screen and dried. The material was then re-sieved through a fine mesh screen, and blended with magnesium stearate and lactose, followed by tableting to create tablets. Quantities of each component in each of the tablet formulations are given below (mg).

| Naproxen SDI | Klucel ® HPC | Methocel ® HPMC | Lactose | Mg Stearate |
|---|---|---|---|---|
| 292.5 | 150 | 0 | 300 | 7.5 |
| 292.5 | 0 | 150 | 300 | 7.5 |

Figure 8:
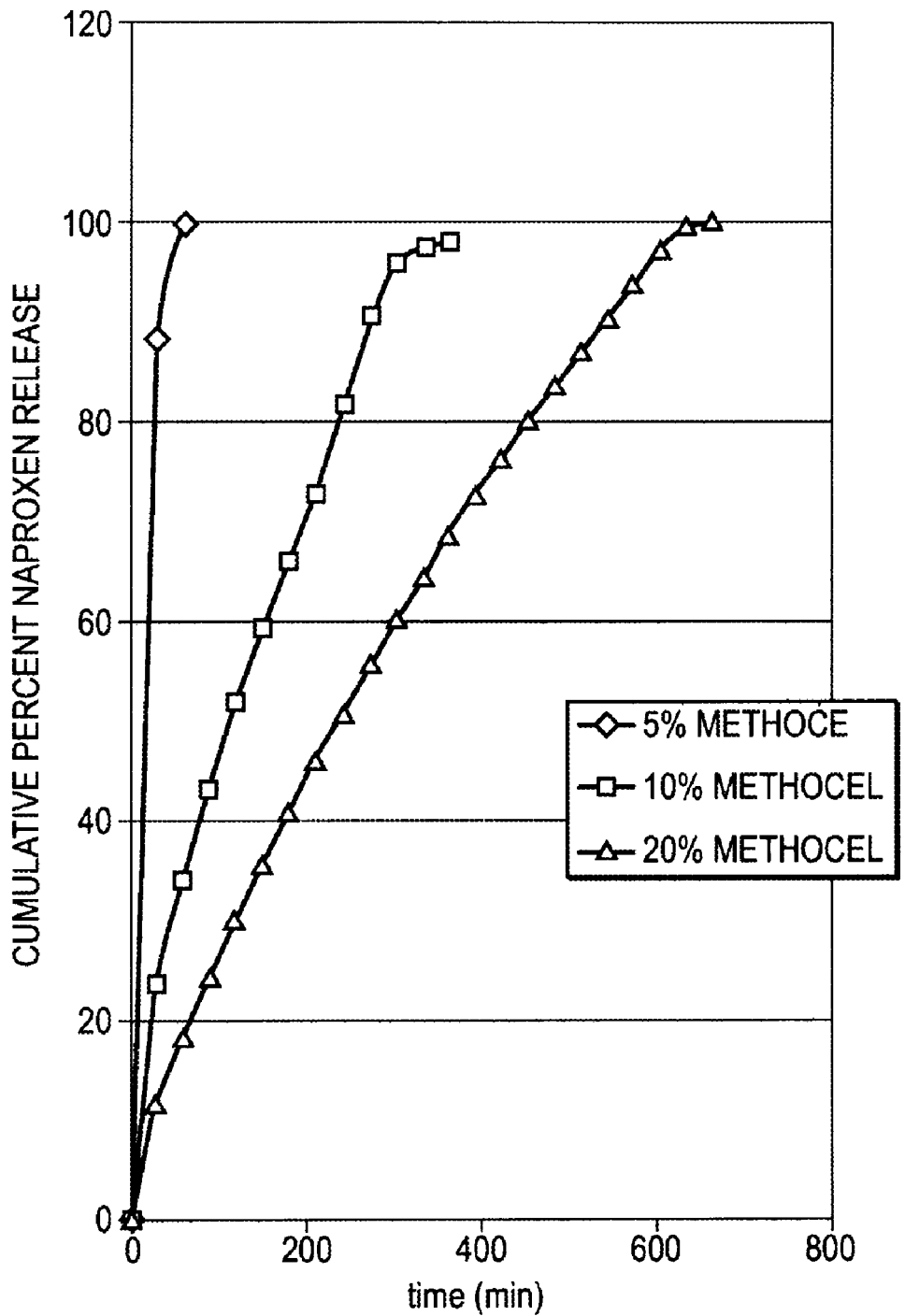
FIG. 8: Shows a graph comparing the cumulative % drug (naproxen) released over time for directly compressed and wet granulated nanoparticulate formulations of Klucel® and Methocel®.

The results, shown in FIG. 8, indicate that for both rate-controlling polymers, Klucel® HPC and Methocel® HPMC, the tablets formed from wet granulation showed a much more controlled release than the normal dry mixture. The prolonged controlled release is likely due to the strong binding of the granules formed by the wet granulation technique. This binding is stronger than the binding of the materials by direct compression. Thus, wet granulation improves controlled release.

EXAMPLE 10

The purpose of this example was to prepare a controlled release formulation of glipizide. Glipizide, also known as 1-cyclohexyl-3[[p-[2-[(5-methylpyrazine-carboxyamido)ethyl]-phenyl]-sulfonyl]-urea, is an oral sulfonylurea.

Glipizide and HPC-SL in the ratio of 10:3, were milled in a Dyno-mill to produce a nanoparticulate glipizide dispersion. The composition was milled for 6 hours, and the average effective particle size of the glipizde was about 177 nm, with about 50% of the particles having a size less than about 157 nm, and about 90% of the particles having a size less than about 276 nm.

The nanoparticulate glipizide suspension was spray dried using a Yamato GB-22® spray-dryer under following conditions to produce a spray-dried glipizide intermediate (SDI):

| | |
|---|---|
| Inlet temp.: | 115° C. |
| Outlet temp.: | 50° C. |
| drying air | 0.36 $m^3$/min |
| atomizing air | 2.5 Kgf/$cm^2$ |

The powder blend for the tablets comprised: 13 mg SDI, 241.6 mg Methocel® (K100LV), 483.3 mg lactose (Foremost #316), and 12.1 mg magnesium stearate, for a total of 750.0 mg. Each 750.0 mg tablet contained 10 mg of the drug (glipizide) The excipients were sieved, blended, and compressed using a Carver press at 5,000 lb for 10 sec. The tablets were analyzed (at 274 nm) using the dissolution system as described above.

Figure 9:
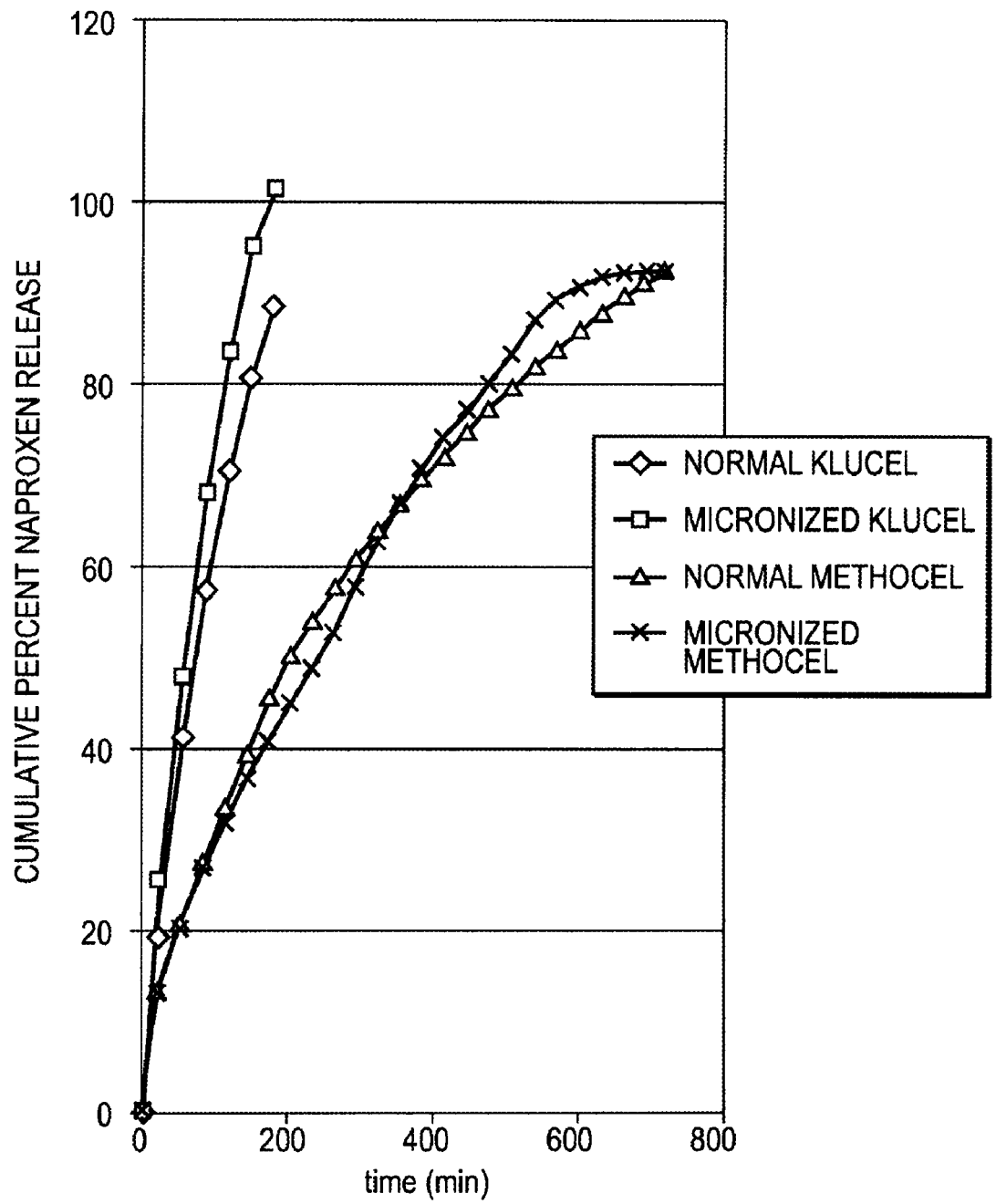
FIG. 9: Shows the controlled release of nanoparticulate glipizide from directly compressed Methocel® tablets.

The results, shown in FIG. 9, indicate a steady release of drug over a time period of just under 16 hours (i.e., about 950 minutes).

In Examples 11-15, all percentages are by weight unless otherwise stated. The term "purified water" refers to water which has been passed through a water filtration system.

EXAMPLE 11

The purpose of this example was to prepare an uncoated controlled release tablet formulation containing nanoparticulate nifedipine.

A colloidal dispersion of nifedipine in water was prepared. The dispersion contained 10% (w/w) of the drug and 2% hydroxypropyl cellulose. Particle size analysis, performed using a Malvern Mastersizer S2.14 (Malvern Instruments Ltd., Malvern, Worcestershire, UK) recorded by a wet method using a 150 ml flow through cell, revealed the following particle size characteristics: $D_{v,90}$ 620 nm; $D_{v,50}$ 313 nm; $D_{v,10}$ 170 nm, with 97.47% of the colloidal particles being less than 1.03 μm in diameter. (Where $D_{v,90}$ 620 nm indicates that 90% of particles had a size less than 620 nm, etc.).

The nifedipine dispersion was prepared for spray drying by a series of four homogenization steps. The dispersion was homogenized at medium shear for 5 min. Sodium lauryl sulphate (0.05%) was added prior to homogenization at medium shear for a further 5 min. The dispersion was then diluted 50:50 with purified water and homogenized at medium shear for a further 10 min. Finally, mannitol (10%) was added and the mixture was homogenized at high shear for 15 min. The final content of the mixture to be spray dried is given in Table 1.

TABLE 1

Composition prior to spray drying for Example 11

| Ingredient | Amount (% by wt.) |
|---|---|
| Nifedipine dispersion | 45.44 |
| Purified water | 45.44 |
| Mannitol | 9.09 |
| Sodium lauryl sulphate | 0.02 |

The mixture thus obtained was spray dried using a Büchi Mini B-191 Spray Drier system (Büchi, Switzerland). The spray drying conditions are summarized in Table 2. The spray dried nifedipine particles thus prepared were then blended. The blend formulation is given in Table 3.

TABLE 2

Spray drying conditions for Example 11

| Parameter | Level |
| --- | --- |
| Inlet temperature | 135° C. |
| Atomising pressure setting | 800 l/min |
| Vacuum pressure | 30-45 mbar |
| Aspirator setting | 100% |
| Spray rate | 6 ml/min |

The blend obtained after the previous step was tableted manually using a Fette E1 tablet press (Wilheim Fette GmbH, Schwarzembek, Germany) fitted with 11 mm round normal concave tooling. The tablets produced had a mean tablet hardness of 122.7 N and a mean tablet potency of 29.7 mg/tablet. In vitro dissolution was carried out in phosphate-citrate buffer, pH 6.8, containing 0.5% sodium lauryl sulphate, using USP apparatus II (100 rpm). Dissolution data is given in Table 4.

TABLE 3

Blend formulation for Example 11

| Ingredient | Amount |
| --- | --- |
| Spray dried nifedipine | 17.92 |
| Avicel PH102 | 30.01 |
| Pharmatose DCL | 30.01 |
| Methocel K 15M | 20.00 |
| Colloidal silicon dioxide | 1.20 |
| Magnesium stearate | 0.86 |

TABLE 4

Dissolution data for uncoated nifedipine tablets prepared according to Example 11

| Time (hr) | % Active Released |
| --- | --- |
| 1.0 | 17.8 |
| 2.0 | 24.9 |
| 4.0 | 37.1 |
| 6.0 | 49.1 |
| 8.0 | 61.5 |
| 10.0 | 71.5 |
| 22.0 | 108.8 |

EXAMPLE 12

The purpose of this example was to prepare a coated controlled release tablet formulation containing nanoparticulate nifedipine.

Tablets prepared according to Example 11 were coated with a Eudragit® L coating solution detailed in Table 5. Coating was performed using an Manesty Accelacota 10" apparatus (Manesty Machine Ltd., Liverpool, UK) and a coating level of 5.5% solids weight gain was achieved. Coating conditions are given in Table 6.

TABLE 5

Coating solution formulation

| Ingredient | Amount (%) |
| --- | --- |
| Eudargit ® L 12.5 | 49.80 |
| Talc | 2.49 |
| Dibutyl sebecate | 1.25 |
| Isopropyl alcohol | 43.46 |
| Purified water | 3.00 |

TABLE 6

Coating conditions

| Parameter | Level |
| --- | --- |
| Inlet temperature | 35-45° C. |
| Outlet temperature | 32-36° C. |
| Air pressure | 1.4 bar |
| Spray rate | 27 g/min |

In vitro dissolution was carried out according to the same methodology used in Example 1: phosphate - citrate buffer, pH 6.8, containing 0.5% sodium lauryl sulphate, using USP apparatus II (100 rpm). Dissolution data is given in Table 7.

TABLE 7

Dissolution data for coated nifedipine tablets prepared according to Example 12

| Time (hr) | % Active Released |
| --- | --- |
| 1.0 | 4.3 |
| 2.0 | 11.5 |
| 4.0 | 24.0 |
| 6.0 | 38.0 |
| 8.0 | 58.3 |
| 10.0 | 66.4 |
| 22.0 | 99.6 |

Figure 10:
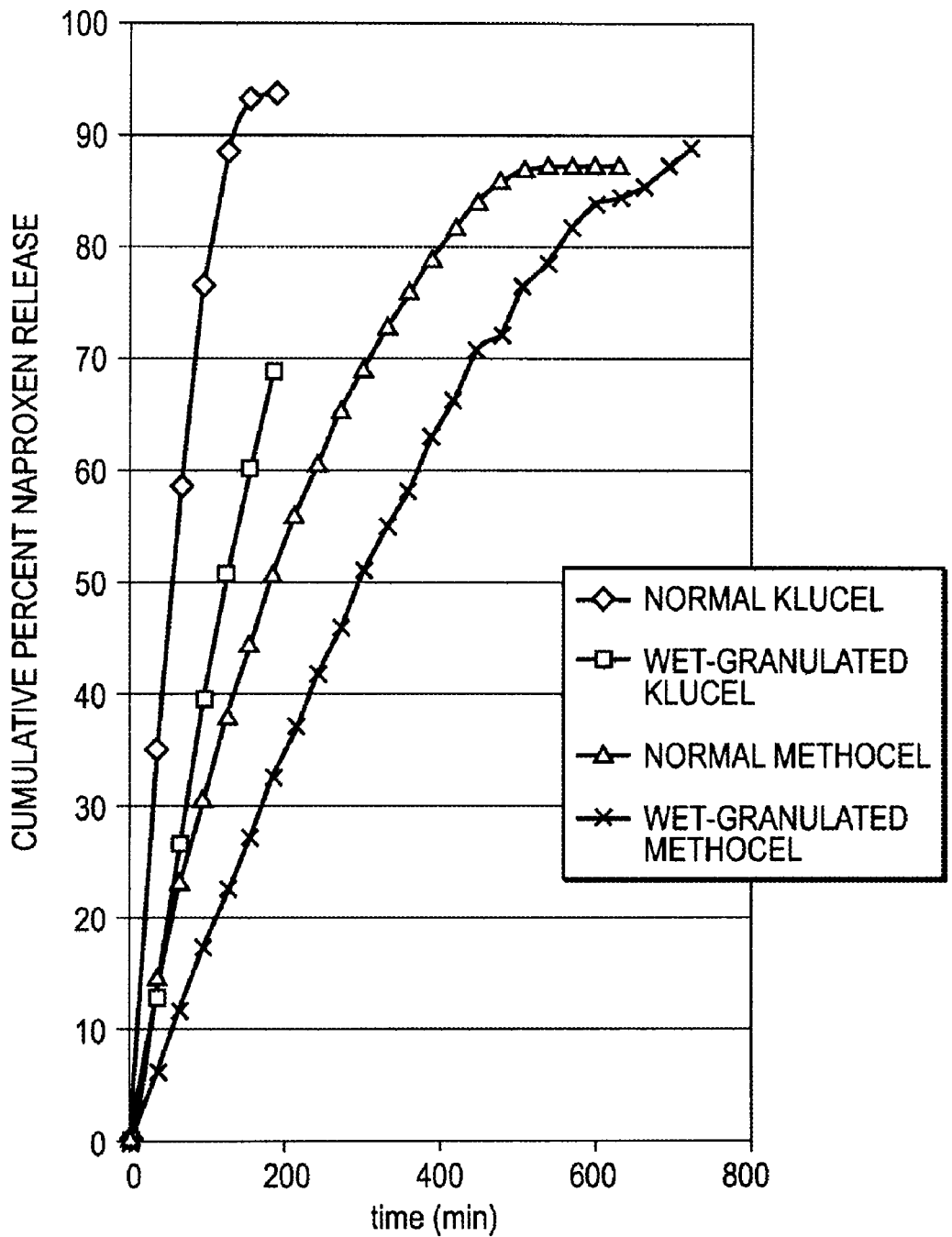
FIG. 10: Shows the mean in vivo plasma profiles of nifedipine after single dosed, fasted, administration in humans for (1) nifedipine containing controlled release matrix tablets coated with a controlled release coating according to the present invention as described in Example 12; and (2) a control composition.

FIG. 10 shows the mean in vivo plasma profiles in nine fasted human volunteers for (1) nifedipine containing controlled release matrix tablets coated with a controlled release coating according to the present invention as described in Example 12; and (2) a control composition. The study had a fully randomized, fully crossed over, single dose administration design. From the figure it can be seen that a controlled release composition prepared according to Example 12 shows a high level of availability and shows good controlled release characteristics over a 24 hour period.

EXAMPLE 13

The purpose of this example was to prepare an uncoated controlled release tablet formulation containing nanoparticulate glipizide.

A colloidal dispersion of glipizide in water was prepared. The dispersion contained 10% (w/w) of the drug and 3% hydroxypropyl cellulose. Particle size analysis, performed using a Malvern Mastersizer S2.14, recorded by a wet method using a 150 ml flow through cell, revealed the following particle size characteristics: $D_{v,90}$ 650 nm; $D_{v,50}$ 386 nm; $D_{v,10}$ 290 nm.

The glipizide dispersion was prepared for spray drying by adding 15% mannitol to the aqueous glipizide dispersion with stirring. The final content of the mixture to be spray dried is given in Table 8.

TABLE 8

Composition prior to spray drying for Example 13

| Ingredient | Amount (% by wt.) |
|---|---|
| Glipizide dispersion | 10 |
| Hydroxypropyl cellulose | 3 |
| Mannitol | 15 |
| Purified water | 72 |

The mixture thus obtained was spray dried using a Büchi Mini B-191 Spray Drier system. The spray drying condition are summarized in Table 9.

TABLE 9

Spray drying conditions for Example 13

| Parameter | Level |
|---|---|
| Inlet temperature | 115-116° C. |
| Atomising pressure setting | 800 mbar |
| Vacuum pressure | 25-45 mbar |
| Aspirator setting | 100% |
| Spray rate | 10 ml/min |

The spray dried glipizide particles thus prepared were then blended. The blend formulation is given in Table 10.

TABLE 10

Blend formulation for Example 13

| Ingredient | Amount (% by wt.) |
|---|---|
| Spray dried glipizide | 3.36 |
| Avicel ™ pH101 | 35.8 |
| Methocel K ™ 100LV | 60.0 |
| Aerosil ™ 200 | 0.4 |
| Magnesium stearate | 0.5 |

The blend obtained after the previous step was tableted using a single station tablet press fitted with 9.5 mm round normal concave tooling. The tablets produced had a mean tablet hardness of 149 N and a mean tablet potency of 9.1 mg/tablet. In vitro dissolution was carried out in $KH_2PO_4$ buffer, pH 7.5, using USP apparatus I (100 rpm). Dissolution data is given in Table 11.

TABLE 11

Dissolution data for uncoated glipizide tablets prepared according to Example 13

| Time (hr) | % Active Released |
|---|---|
| 1.0 | 8.0 |
| 2.0 | 17.0 |
| 4.0 | 35.1 |
| 6.0 | 51.4 |
| 8.0 | 65.2 |
| 10.0 | 79.5 |
| 22.0 | 95.6 |

EXAMPLE 14

The purpose of this example was to prepare delayed release nanoparticulate nifedipine capsules.

A colloidal dispersion of nifedipine in water was prepared. The dispersion contained 10% w/w Nifedipine, 2% hydroxypropylcellulose, and 0.1% Sodium Lauryl Sulphate in water. Particle size analysis, performed using a Malvern Mastersizer S2.14, recorded by a wet method using a 150 ml flow through cell, revealed the following particle size characteristics: Dv,90=490 nm; Dv,50=290 nm; Dv,10=170 nm The nifedipine dispersion was prepared for spray drying by adding Purified Water and homogenizing for 5 minutes. Mannitol was added and the resulting mixture was homogenized for 15 minutes. The final content of the mixture to be spray dried is given in Table 12.

TABLE 12

Composition prior to spray drying for Example 14

| Ingredient | Amount (% by wt.) |
|---|---|
| Nifedipine dispersion | 45.45 |
| Mannitol | 9.09 |
| Purified water | 45.45 |

The mixture thus obtained was spray dried using a Buchi Mini B-191 Spray Drier system. The spray drying conditions are summarized in Table 13.

TABLE 13

Spray drying conditions for Example 14

| Parameter | Level |
|---|---|
| Inlet temperature | 135° C. |
| Atomising pressure setting | 800 mbar |
| Aspirator setting | 100% |
| Flow rate | 6 ml/mm |

The spray dried nifedipine particles thus prepared were then blended. The blend formulation is given in Table 14.

TABLE 14

Blend formulation for Example 14

| Ingredient | Amount (% by wt.) |
|---|---|
| Spray dried nifedipine (Dv,90 ca 500 nm) | 10.40 |
| Avicef ™ pH102 | 77.05 |
| Explotab | 10.00 |
| Colloidal Silicon Dioxide | 1.00 |
| Magnesium stearate | 1.50 |

The resulting blend was tableted using a Fette P2100 rotary tablet press (Wilhelm Fette GmbH, Schwarzenbek, Germany) fitted with 3.8 mm shallow concave multi-tipped tooling. The tablets had a mean set up hardness of 56 N and a mean set up weight of 34.46 mg.

The tablets thus obtained were coated in a Hi-Coater (Vector Corp., Marion, Iowa, USA) with the Eudragit S coating solution detailed in Table 15. A coating level of 10.03% solids weight gain was achieved.

TABLE 15

Coating Solution Formulation for Example 14

| Ingredient | Amount (% by wt.) |
|---|---|
| Eudragit S 12.5 | 50.0 |
| Talc | 2.50 |
| Dibutyl Sebecate | 1.25 |
| Isopropyl Alcohol | 43.25 |
| Purified Water | 3.00 |

The coated minitablets thus obtained were hand-filled into hard gelatin capsules to form Nifedipine 10 mg Capsules (9 minitablets/capsule). In vitro dissolution was carried out in citrate-phosphate buffer, pH 6.8, containing 0.5% Sodium Lauryl Sulphate, using a USP apparatus II (100 rpm). The dissolution data of the resulting capsules is given in Table 16.

TABLE 16

Dissolution data for Nifedipine 10 mg capsules prepared according to Example 14

| Time (hr) | % Active Released |
|---|---|
| 0.25 | 3.99 |
| 0.5 | 4.60 |
| 0.75 | 21.10 |
| 1.0 | 93.07 |
| 1.5 | 100.39 |
| 2.0 | 100.79 |

EXAMPLE 15

The purpose of this example was to prepare a control for delayed release nanoparticulate nifedipine capsules. The control does not contain a nanoparticulate composition.

Nifedipine raw material (Dv,90=673 μm), Explotab, and Avicel pH 102 were mixed in the Gral 25 (NV-Machines Colett SA, Wommelgam, Belgium) for 10 minutes at 1000 rpm. Purified water was gradually added with mixing until granulation was achieved. The granulate was oven dried for 18 hours at 50° C. The dried granulate was milled through a 50 mesh screen using a Fitzmill M5A (The Fitzpatrick Co. Europe, Sint-Niklaas, Belgium). The final content of the granulate is summarized in Table 17.

TABLE 17

Final composition of Granulate for Example 15

| Ingredient | Amount (% by wt.) |
|---|---|
| Nifedipine | 7.68 |
| Explotab | 24.22 |
| Avicel pH 102 | 68.10 |

The granulate thus obtained (Dv,90=186 μm) was then blended. The blend formulation is given in Table 18.

TABLE 18

Blend Formulation for Example 15

| Ingredient | Amount (% by wt.) |
|---|---|
| Nifedipine Granulate (Dv, 90 = 186 μm) | 41.28 |
| Avicel pH102 | 56.22 |
| Colloidal Silicon Dioxide | 1.00 |
| Magnesium Stearate | 1.50 |

The particle size analysis of the starting nifedipine raw material and the milled nifedipine granulate, performed using the Malvern Mastersizer S with a 1000 mm lens (nifedipine raw material) and a 300 mm lens (milled nifedipine granulate) recorded by a dry powder method, revealed the particle size characteristics given in Table 19.

TABLE 19

Particle Size Analysis of Nifedipine Compositions

| Size Range | Raw Nifedipine | Milled Nifedipine Granulate |
|---|---|---|
| Dv, 90 | 673 μm | 186 μm |
| Dv, 50 | 234 μm | 103 μm |
| Dv, 10 | 14 μm | 32 μm |

The resulting blend was tableted using a Fette P2100 rotary tablet press fitted with 3.8 mm shallow concave multi-tipped tooling. The tablets had a mean set up hardness of 47 N and a mean set up weight of 35 mg. The tablets thus obtained were coated in a Hi-Coater with the Eudragit S coating solution detailed in Table 20. A coating level of 10.34% solids weight gain was achieved.

TABLE 20

Coating Solution Formulation for Example 15

| Ingredient | Amount (% by wt.) |
|---|---|
| Eudragit S 12.5 | 50.0 |
| Talc | 2.50 |
| Dibutyl Sebecate | 1.25 |
| Isopropyl Alcohol | 43.25 |
| Purified Water | 3.00 |

The coated minitablets thus obtained were hand-filled into hard gelatin capsules to form nifedipine 10 mg capsules (9 minitablets/capsule). In vitro dissolution was carried out in citrate-phosphate buffer, pH 6.8, containing 0.5% Sodium Lauryl Sulphate, using USP apparatus II (100 rpm). The dissolution data for the resulting capsules is given in Table 21.

TABLE 21

Dissolution data for Nifedipine 10 mg capsules prepared according to Example 15

| Time (hr) | % Active Released |
|---|---|
| 0.25 | 8.83 |
| 0.5 | 32.50 |
| 0.75 | 77.88 |
| 1.0 | 85.26 |
| 1.5 | 91.30 |
| 2.0 | 94.46 |

EXAMPLE 16

Figure 11:
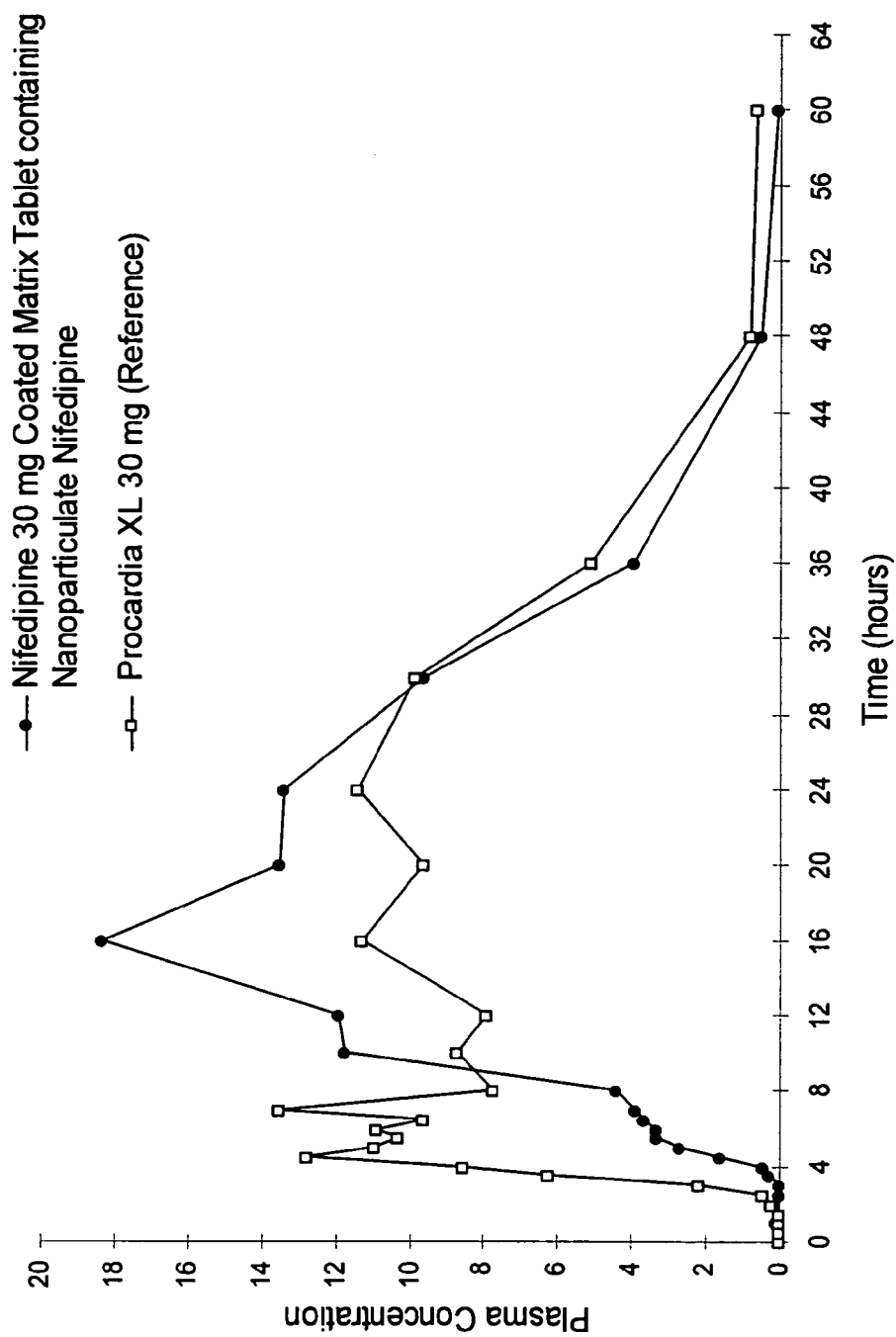
FIG. 11: Shows the mean in vivo plasma profiles of nifedipine after single dosed, fasted, administration in humans for (1) a nifedipine controlled release composition manufactured according to the present invention as described in Example 14; and (2) a control composition.
Figure 12:
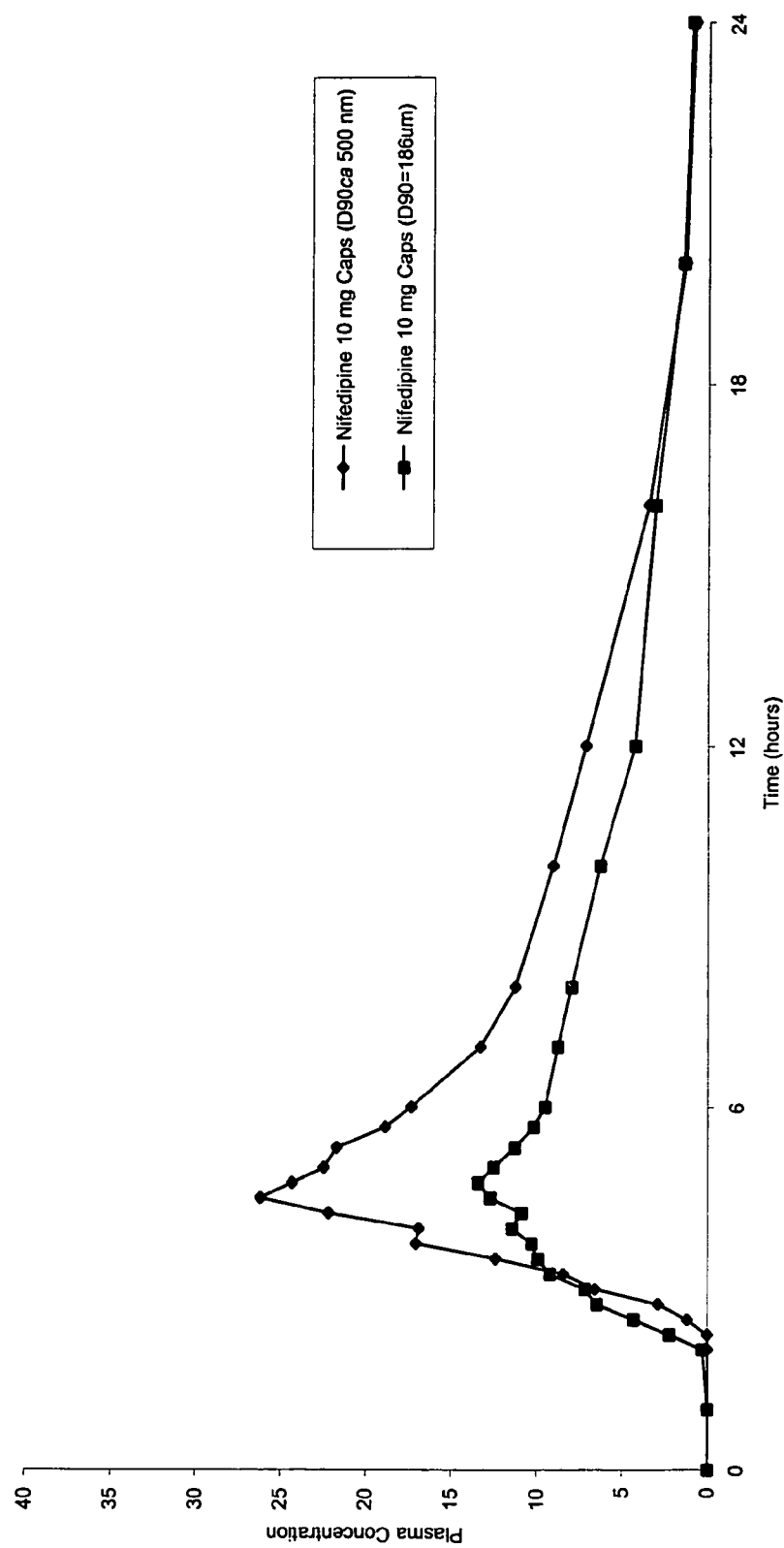
FIG. 12: Depicts the comparison of the plasma concentration of nifedipine having a $D_{90}$ particle size of 500 nm with that of nifedipine having a $D_{90}$ particle size of 186 μm over a period of 24 hours after administration.

FIG. 11 shows the mean in-vivo plasma profiles of nifedipine in ten fasted human volunteers for (1) a controlled release composition manufactured according to the present invention as described in Example 14 (nifedipine 10 mg capsules (Dv,90 ca 500 nm)); and (2) a control composition manufactured as described in Example 15 (nifedipine 10 mg capsules (Dv,90=186 μm)). The study had a single dose, fully randomized, fully crossed over, oral administration design. From the Figure it can be seen that the controlled release composition manufactured according to the present invention shows an initial lag time followed by a rapid and high level of availability of active.

It should be noted that the controlled release composition manufactured in accordance with the invention showed a relative bioavailability of 1.45 (i.e., 45% enhanced bioavailability as compared with the control).

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

We claim:

1. A solid dose controlled release nanoparticulate composition consisting of:
   (a) a poorly soluble nanoparticulate drug and at least one surface stabilizer associated with the surface of the nanoparticulate drug, wherein at least 50% of the drug particles have an average particle size of less than about 1000 nm when measured by light scattering techniques, and
   (b) a rate controlling matrix consists of at least one pharmaceutically acceptable high molecular weight rate-controlling polymer, wherein:
      (i) the nanoparticulate drug and the surface stabilizer associated with the surface thereof are dispersed in the high molecular weight rate-controlling polymer throughout the rate controlling matrix,
      (ii) the controlled release nanoparticulate composition provides controlled release of the nanoparticulate drug for a time period ranging from about 2 to about 24 hours,
      (iii) the concentration of the high molecular weight rate controlling polymer is from about 5 to about 95% (w/w),
      (iv) the surface stabilizer is selected from the group consisting of gelatin, lecithin, dextran, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethylcellulose phthalate, noncrystalline cellulose, magnesium aluminum silicate, triethanolamine, polyvinyl alcohol, polyvinylpyrrolidone, tyloxapol, poloxamers, poloxamines, poloxamine 908, dialkylesters of sodium sulfosuccinic acid, sodium lauryl sulfate, an alkyl aryl polyether sulfonate, a mixture of sucrose stearate and sucrose distearate, p-isononylphenoxypoly-(glycidol), SA9OHCO, decanoyl-N-methylglucamide, n-decyl -D-glucopyranoside, n-decyl -D-maltopyranoside, n-dodecyl -D-glucopyranoside, n-dodecyl -D-maltoside, heptanoyl-N-methylglucamide, n-heptyl—D-glucopyranoside, n-heptyl -D-thioglucoside, n-hexyl -D-glucopyranoside, nonanoyl-N-methylglucamide, n-noyl -D-glucopyranoside, octanoyl-N-methylglucamide, n-octyl—D-glucopyranoside, and octyl -D-thioglucopyranoside, and
      (v) the high molecular weight rate-controlling polymer is selected from the group consisting of polyethylene oxide (PEO), polyvinyl acetate phthalate, gum arabic, agar, guar gum, cereal gums, dextran, casein, gelatin, pectin, carrageenan, waxes, shellac, hydrogenated vegetable oils, polyvinylpyrrolidone, hydroxypropyl cellulose (HPC), hydroxyethyl cellulose (HEC), hydroxypropyl methylcelluose (HPMC), sodium carboxymethylcellulose (CMC), poly(ethylene) oxide, alkyl cellulose, ethyl cellulose, methyl cellulose, carboxymethyl cellulose, hydrophilic cellulose derivatives, polyethylene glycol, polyvinylpyrrolidone, cellulose acetate, cellulose acetate butyrate, cellulose acetate phthalate, cellulose acetate trimellitate, polyvinyl acetate phthalate, hydroxypropylmethyl cellulose phthalate, hydroxypropylmethyl cellulose acetate succinate, polyvinyl acetaldiethylamino acetate, poly(alkylmethacrylate), poly(vinyl acetate), polymers derived from acrylic or methacrylic acid and their respective esters, and copolymers derived from acrylic or methacrylic acid and their respective esters.

2. The solid dose controlled release nanoparticulate composition of claim 1, wherein the effective average particle size of the nanoparticulate drug is selected from the group consisting of less than about 800 nm, less than about 600 nm, less than about 400 nm, less than about 300 nm, less than about 250 nm, less than about 100 nm, and less than about 50 nm, wherein at least 50% of the drug particles have an average particle size of less than about 800, 600, 400, 300, 250, 100, or 50 nm, respectively, when measured by light scattering techniques.

3. The solid dose controlled release nanoparticulate composition of claim 1, wherein the concentration of the high molecular weight rate controlling polymer is from about 10 to about 65% (w/w).

4. The solid dose controlled release nanoparticulate composition of claim 1, wherein the solid dose formulation is made by wet granulation.

5. The solid dose controlled release nanoparticulate composition of claim 1 formed by wet granulation, wherein water is added to the nanoparticulate drug, surface stabilizer, and polymer to form granules prior to forming the solid dose of the controlled release formulation.

6. The solid dose controlled release nanoparticulate composition of claim 1, wherein the high molecular weight rate-controlling polymer is hydroxypropylmethyl cellulose (HPMC).

7. The solid dose controlled release nanoparticulate composition of claim 1, wherein the poorly water soluble nanoparticulate drug is present in an amount of from about 1 µg to about 800 mg.

8. A solid dosage form consisting of the controlled release nanoparticulate composition according to claim 1 and at least one auxiliary excipient, wherein the solid dosage form is in a tablet form, a multiparticulate form, or a powder form.

9. The solid dosage form of claim 8, wherein the controlled release nanoparticulate composition and the at least one auxiliary excipient are compressed to form a tablet.

10. The solid dosage form of claim 8, wherein the controlled release nanoparticulate composition and the at least one auxiliary excipient are compressed to form a multilayer tablet.

11. A method of preparing a solid dose controlled release nanoparticulate formulation comprising:
    (a) combining a nanoparticulate composition of a nanoparticulate drug, at least one surface stabilizer associated with the surface of the nanoparticulate drug, wherein at least 50% of the drug particles have an average particle size of less than about 1000 nm when measured by light scattering techniques, and at least one pharmaceutically acceptable high molecular weight rate-controlling polymer at a concentration of from about 5% to about 95% (w/w);
    (b) forming a solid dose formulation from the mixture of step (a); wherein the high molecular weight rate-controlling polymer forms a rate controlling matrix, and the nanoparticulate drug and the surface stabilizer associated with the surface thereof are dispersed throughout the rate controlling matrix, and (c) selecting the solid dose formulation which has a controlled release of the nanoparticulate drug following administration for a time period ranging from about 2 to about 24 hours, wherein the solid dose controlled release nanoparticulate composition consists of:

(1) the nanoparticulate drug and the surface stabilizer associated with the surface of the nanoparticulate drug, wherein at least 50% of the drug particles have an average particle size of less than about 1000 nm when measured by light scattering techniques, and (2) a rate controlling matrix comprised of at least the high molecular weight rate-controlling polymer, wherein:

(i) the nanoparticulate drug and the surface stabilizer associated with the surface thereof are dispersed in the high molecular weight rate-controlling polymer throughout the rate controlling matrix, (ii) the concentration of the high molecular weight rate controlling polymer is from about 5 to about 95% (w/w), (iii) the surface stabilizer is selected from the group consisting of gelatin, lecithin, dextran, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethylcellulose phthalate, noncrystalline cellulose, magnesium aluminum silicate, triethanolamine, polyvinyl alcohol, polyvinylpyrrolidone, tyloxapol, poloxamers, poloxamines, poloxamine 908, dialkylesters of sodium sulfosuccinic acid, sodium lauryl sulfate, an alkyl aryl polyether sulfonate, a mixture of sucrose stearate and sucrose distearate, p-isononylphenoxypoly-(glycidol), SA9OHCO, decanoyl-N-methylglucamide, n-decyl -D-glucopyranoside, n-decyl -D-maltopyranoside, n-dodecyl -D-glucopyranoside, n-dodecyl -D-maltoside, heptanoyl-N-methylglucamide, n-heptyl—D-glucopyranoside, n-heptyl -D-thioglucoside, n-hexyl -D-glucopyranoside, nonanoyl-N-methylglucamide, n-noyl -D-glucopyranoside, octanoyl-N-methylglucamide, n-octyl—D-glucopyranoside, and octyl -D-thioglucopyranoside, wherein the nanoparticulate drug is in a crystalline phase, an amorphous phase, or a mixture thereof, and (iv) wherein the high molecular weight rate-controlling polymer is selected from the group consisting of polyethylene oxide (PEO), polyvinyl acetate phthalate, gum arabic, agar, guar gum, cereal gums, dextran, casein, gelatin, pectin, carrageenan, waxes, shellac, hydrogenated vegetable oils, polyvinylpyrrolidone, hydroxypropyl cellulose (HPC), hydroxyethyl cellulose (HEC), hydroxypropyl methylcelluose (HPMC), sodium carboxymethylcellulose (CMC), poly(ethylene) oxide, alkyl cellulose, ethyl cellulose, methyl cellulose, carboxymethyl cellulose, hydrophilic cellulose derivatives, polyethylene glycol, polyvinylpyrrolidone, cellulose acetate, cellulose acetate butyrate, cellulose acetate phthalate, cellulose acetate trimellitate, polyvinyl acetate phthalate, hydroxypropylmethyl cellulose phthalate, hydroxypropylmethyl cellulose acetate succinate, polyvinyl acetaldiethylamino acetate, poly(alkylmethacrylate), poly(vinyl acetate), polymers derived from acrylic or methacrylic acid and their respective esters, and copolymers derived from acrylic or methacrylic acid and their respective esters.

12. The method of claim 11, wherein the effective average particle size of the nanoparticulate drug particles is selected from the group consisting of less than about 800 nm, less than about 600 nm, less than about 400 nm, less than about 300 nm, less than about 250 nm, less than about 100 nm, and less than about 50 nm, wherein at least 50% of the drug particles have an average particle size of less than about 800, 600, 400, 300, 250, 100, or 50 nm, respectively, when measured by light scattering techniques.

13. The method of claim 11, wherein the concentration of the high molecular weight rate-controlling polymer is from about 10 to about 65% (w/w).

14. The method of claim 12, comprising adding water to the nanoparticulate drug, surface stabilizer, and high molecular weight rate-controlling polymer to form granules prior to step (b).

15. A method of treating a mammal comprising administering to the mammal an effective amount of a solid dose controlled release nanoparticulate formulation composition, wherein the composition consists of:

(a) the formulation consists of a poorly soluble nanoparticulate drug particles and at least one surface stabilizer associated with the surface of the nanoparticulate drug, wherein at least 50% of the drug particles have an average particle size of less than about 1000 nm when measured by light scattering techniques, and (b) a rate controlling matrix consists of at least one pharmaceutically acceptable high molecular weight rate-controlling polymer, wherein:

(i) at a concentration of from about 5% to about 95% (w/w), wherein the nanoparticulate drug and the surface stabilizer associated with the surface thereof are dispersed in the high molecular weight rate-controlling polymer throughout the rate controlling matrix;

(ii) the formulation has a controlled release of the nanoparticulate drug following administration composition provides controlled release of the nanoparticulate drug for a time period ranging from about 2 to about 24 hours, (iii) the concentration of the high molecular weight rate controlling polymer is from about 5 to about 95% (w/w), (iv) wherein the surface stabilizer is selected from the group consisting of gelatin, lecithin, dextran, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethyl-cellulose phthalate, noncrystalline cellulose, magnesium aluminum silicate, triethanolamine, polyvinyl alcohol, polyvinylpyrrolidone, tyloxapol, poloxamers, poloxamines, poloxamine 908, dialkylesters of sodium sulfosuccinic acid, sodium lauryl sulfate, an alkyl aryl polyether sulfonate, a mixture of sucrose stearate and sucrose distearate, p-isononylphenoxypoly-(glycidol), SA9OHCO, decanoyl-N-methylglucamide, n-decyl -D-glucopyranoside, n-decyl -D-maltopyranoside, n-dodecyl -D-glucopyranoside, n-dodecyl -D-maltoside, heptanoyl-N-methylglucamide, n-heptyl—D-glucopyranoside, n-heptyl -D-thioglucoside, n-hexyl -D-glucopyranoside, nonanoyl-N-methylglucamide, n-noyl -D-glucopyranoside, octanoyl-N-methylglucamide, n-octyl—D-glucopyranoside, and octyl -D-thioglucopyranoside, wherein the nanoparticulate drug is in a crystalline phase, an amorphous phase, or a mixture thereof, and
(v) wherein the high molecular weight rate-controlling polymer is selected from the group consisting of polyethylene oxide (PEO), polyvinyl acetate phthalate, gum arabic, agar, guar gum, cereal gums, dextran, casein, gelatin, pectin, carrageenan, waxes, shellac, hydrogenated vegetable oils, polyvinylpyrrolidone, hydroxypropyl cellulose (HPC), hydroxyethyl cellulose (HEC), hydroxypropyl methylcelluose (HPMC), sodium carboxymethylcellulose (CMC), poly(ethylene) oxide, alkyl cellulose, ethyl cellulose, methyl cellulose, carboxymethyl cellulose, hydrophilic cellulose derivatives, polyethylene glycol, polyvinylpyrrolidone, cellulose acetate, cellulose acetate butyrate, cellulose acetate phthalate, cellulose acetate trimellitate, polyvinyl acetate phthalate, hydroxypropylmethyl cellulose phthalate, hydroxypropylmethyl cellulose acetate succinate, polyvinyl acetaldiethylamino acetate, poly(alkylmethacrylate), poly(vinyl acetate), polymers derived from acrylic or methacrylic acid and their respective esters, and copolymers derived from acrylic or methacrylic acid and their respective esters.

16. The method of claim 15, wherein the effective average particle size of the nanoparticulate drug particles is selected from the group consisting of less than about 800 nm, less than about 600 nm, less than about 400 nm, less than about 300 nm, less than about 250 nm, less than about 100 nm, and less than about 50 nm, wherein at least 50% of the drug particles have an average particle size of less than about 800, 600, 400, 300, 250, 100, or 50 nm, respectively, when measured by light scattering techniques.

17. The solid dose controlled release nanoparticulate composition of claim 1, wherein the drug is selected from the group consisting of analgesics, anti-inflammatory agents, anthelmintics, anti-arrhythmic agents, antiasthma agents, antibiotics, anticoagulants, antidepressants, antidiabetic agents, antiepileptics, antihistamines, antitussives, antihypertensive agents, antimuscarinic agents, antimycobacterial agents, antineoplastic agents, antipyretics, immunosuppressants, immunostimulants, antithyroid agents, antiviral agents, anxiolytic sedatives, astringents, beta-adrenoceptor blocking agents, blood products and substitutes, bronchodilators, cardiac inotropic agents, chemotherapeutics, contrast media, corticosteroids, cough suppressants, diagnostic agents, diagnostic imaging agents, diuretics, dopaminergics, haemostatics, immunological agents, lipid regulating agents, muscle relaxants, proteins, polypeptides, parasympathomimetics, parathyroid calcitonin and biphosphonates, prostaglandins, radio-pharmaceuticals, hormones, sex hormones, anti-allergic agents, stimulants, anoretics, sympathomimetics, thyroid agents, vaccines, vasodilators, and xanthines.

18. The solid dose controlled release nanoparticulate composition of claim 1, wherein the drug is selected from the group consisting of alprazolam, amiodarone, amlodipine, astemizole, atenolol, azathioprine, azelatine, beclomethasone, budesonide, buprenorphine, butalbital, carbamazepine, carbidopa, cefotaxime, cephalexin, cholestyramine, ciprofloxacin, cisapride, cisplatin, clarithromycin, clonazepam, clozapine, cyclosporin, diazepam, diclofenac sodium, digoxin, dipyridamole, divalproex, dobutamine, doxazosin, enalapril, estradiol, etodolac, etoposide, famotidine, felodipine, fentanyl citrate, fexofenadine, finasteride, fluconazole, flunisolide, flurbiprofen, fluvoxamine, furosemide, glipizide, gliburide, ibuprofen, isosorbide dinitrate, isotretinoin, isradipine, itraconazole, ketoconazole, ketoprofen, lamotrigine, lansoprazole, loperamide, loratadine, lorazepam, lovastatin, medroxyprogesterone, mefenamic acid, methylprednisolone, midazolam, mometasone, nabumetone, naproxen, nicergoline, nifedipine, norfloxacin, omeprazole, paclitaxel, phenytoin, piroxicam, quinapril, ramipril, risperidone, sertraline, simvastatin, terbinafine, terfenadine, triamcinolone, valproic acid, zolpidem, and pharmaceutically acceptable salts thereof 19. The solid dose controlled release nanoparticulate composition of claim 1, wherein the drug is selected from the group consisting of naproxen, glipizide, and nifedipine.

20. The solid dosage form of claim 8, wherein the drug is selected from the group consisting of analgesics, anti-inflammatory agents, anthelmintics, anti-arrhythmic agents, antiasthma agents, antibiotics, anticoagulants, antidepressants, antidiabetic agents, antiepileptics, antihistamines, antitussives, antihypertensive agents, antimuscarinic agents, antimycobacterial agents, antineoplastic agents, antipyretics, immunosuppressants, immunostimulants, antithyroid agents, antiviral agents, anxiolytic sedatives, astringents, beta-adrenoceptor blocking agents, blood products and substitutes, bronchodilators, cardiac inotropic agents, chemotherapeutics, contrast media, corticosteroids, cough suppressants, diagnostic agents, diagnostic imaging agents, diuretics, dopaminergics, haemostatics, immunological agents, lipid regulating agents, muscle relaxants, proteins, polypeptides, parasympathomimetics, parathyroid calcitonin and biphosphonates, prostaglandins, radio-pharmaceuticals, hormones, sex hoimones, anti-allergic agents, stimulants, anoretics, sympathomimetics, thyroid agents, vaccines, vasodilators, and xanthines.

21. The solid dosage form of claim 8, wherein the drug is selected from the group consisting of alprazolam, amiodarone, amlodipine, astemizole, atenolol, azathioprine, azelatine, beclomethasone, budesonide, buprenorphine, butalbital, carbamazepine, carbidopa, cefotaxime, cephalexin, cholestyramine, ciprofloxacin, cisapride, cisplatin, clarithromycin, clonazepam, clozapine, cyclosporin, diazepam, diclofenac sodium, digoxin, dipyridamole, divalproex, dobutamine, doxazosin, enalapril, estradiol, etodolac, etoposide, famotidine, felodipine, fentanyl citrate, fexofenadine, finasteride, fluconazole, flunisolide, flurbiprofen, fluvoxamine, furosemide, glipizide, gliburide, ibuprofen, isosorbide dinitrate, isotretinoin, isradipine, itraconazole, ketoconazole, ketoprofen, lamotrigine, lansoprazole, loperamide, loratadine, lorazepam, lovastatin, medroxyprogesterone, mefenamic acid, methylprednisolone, midazolam, mometasone, nabumetone, naproxen, nicergoline, nifedipine, norfloxacin, omeprazole, paclitaxel, phenytoin, piroxicam, quinapril, ramipril, risperidone, sertraline, simvastatin, terbinafine, terfenadine, triamcinolone, valproic acid, zolpidem, and pharmaceutically acceptable salts thereof.

22. The solid dosage form of claim 8, wherein the drug is selected from the group consisting of naproxen, glipizide, and nifedipine.

23. The method of claim 11, wherein the drug is selected from the group consisting of analgesics, anti-inflammatory agents, anthelmintics, anti-arrhythmic agents, antiasthma agents, antibiotics, anticoagulants, antidepressants, antidiabetic agents, antiepileptics, antihistamines, antitussives, antihypertensive agents, antimuscarinic agents, antimycobacterial agents, antineoplastic agents, antipyretics, immunosuppressants, immunostimulants, antithyroid agents, antiviral agents, anxiolytic sedatives, astringents, beta-adrenoceptor blocking agents, blood products and substitutes, bronchodilators, cardiac inotropic agents, chemotherapeutics, contrast media, corticosteroids, cough suppressants, diagnostic agents, diagnostic imaging agents, diuretics, dopaminergics, haemostatics, immunological agents, lipid regulating agents, muscle relaxants, proteins, polypeptides, parasympathomimetics, parathyroid calcitonin and biphosphonates, prostaglandins, radio-pharmaceuticals, hormones, sex hormones, anti-allergic agents, stimulants, anoretics, sympathomimetics, thyroid agents, vaccines, vasodilators, and xanthines.

24. The method of claim 11, wherein the drug is selected from the group consisting of alprazolam, amiodarone, amlodipine, astemizole, atenolol, azathioprine, azelatine, beclomethasone, budesonide, buprenorphine, butalbital, carbamazepine, carbidopa, cefotaxime, cephalexin, cholestyramine, ciprofloxacin, cisapride, cisplatin, clarithromycin, clonazepam, clozapine, cyclosporin, diazepam, diclofenac sodium, digoxin, dipyridamole, divalproex, dobutamine, doxazosin, enalapril, estradiol, etodolac, etoposide, famotidine, felodipine, fentanyl citrate, fexofenadine, finasteride, fluconazole, flunisolide, flurbiprofen, fluvoxamine, furosemide, glipizide, gliburide, ibuprofen, isosorbide dinitrate, isotretinoin, isradipine, itraconazole, ketoconazole, ketoprofen, lamotrigine, lansoprazole, loperamide, loratadine, lorazepam, lovastatin, medroxyprogesterone, mefenamic acid, methylprednisolone, midazolam, mometasone, nabumetone, naproxen, nicergoline, nifedipine, norfloxacin, omeprazole, paclitaxel, phenytoin, piroxicam, quinapril, ramipril, risperidone, sertraline, simvastatin, terbinafine, terfenadine, triamcinolone, valproic acid, zolpidem, and pharmaceutically acceptable salts thereof.

25. The method of claim 11, wherein the drug is selected from the group consisting of naproxen, glipizide, and nifedipine.

26. The method of claim 15, wherein the drug is selected from the group consisting of analgesics, anti-inflammatory agents, anthelmintics, anti-arrhythmic agents, antiasthma agents, antibiotics, anticoagulants, antidepressants, antidiabetic agents, antiepileptics, antihistamines, antitussives, antihypertensive agents, antimuscarinic agents, antimycobacterial agents, antineoplastic agents, antipyretics, immunosuppressants, immunostimulants, antithyroid agents, antiviral agents, anxiolytic sedatives, astringents, beta-adrenoceptor blocking agents, blood products and substitutes, bronchodilators, cardiac inotropic agents, chemotherapeutics, contrast media, corticosteroids, cough suppressants, diagnostic agents, diagnostic imaging agents, diuretics, dopaminergics, haemostatics, immunological agents, lipid regulating agents, muscle relaxants, proteins, polypeptides, parasympathomimetics, parathyroid calcitonin and biphosphonates, prostaglandins, radio-pharmaceuticals, hormones, sex hormones, anti-allergic agents, stimulants, anoretics, sympathomimetics, thyroid agents, vaccines, vasodilators, and xanthines.

27. The method of claim 15, wherein the drug is selected from the group consisting of alprazolam, amiodarone, amlodipine, astemizole, atenolol, azathioprine, azelatine, beclomethasone, budesonide, buprenorphine, butalbital, carbamazepine, carbidopa, cefotaxime, cephalexin, cholestyramine, ciprofloxacin, cisapride, cisplatin, clarithromycin, clonazepam, clozapine, cyclosporin, diazepam, diclofenac sodium, digoxin, dipyridamole, divalproex, dobutamine, doxazosin, enalapril, estradiol, etodolac, etoposide, famotidine, felodipine, fentanyl citrate, fexofenadine, finasteride, fluconazole, flunisolide, flurbiprofen, fluvoxamine, furosemide, glipizide, gliburide, ibuprofen, isosorbide dinitrate, isotretinoin, isradipine, itraconazole, ketoconazole, ketoprofen, lamotrigine, lansoprazole, loperamide, loratadine, lorazepam, lovastatin, medroxyprogesterone, mefenamic acid, methylprednisolone, midazolam, mometasone, nabumetone, naproxen, nicergoline, nifedipine, norfloxacin, omeprazole, paclitaxel, phenytoin, piroxicam, quinapril, ramipril, risperidone, sertraline, simvastatin, terbinafine, terfenadine, triamcinolone, valproic acid, zolpidem, and pharmaceutically acceptable salts thereof.

28. The method of claim 15, wherein the drug is selected from the group consisting of naproxen, glipizide, and nifedipine.

\* \* \* \* \*